(12) United States Patent
Cros et al.

(10) Patent No.: US 11,684,276 B2
(45) Date of Patent: **\*Jun. 27, 2023**

(54) IMPLANTABLE WIRELESS PRESSURE SENSOR

(71) Applicant: TC1 LLC, Wilmington, DE (US)

(72) Inventors: Florent Cros, Decatur, GA (US); David O'Brien, Atlanta, GA (US); Michael Fonseca, Marietta, GA (US); Matthew Abercrombie, Marietta, GA (US); Jin Woo Park, Suwanee, GA (US); Angad Singh, Marietta, GA (US)

(73) Assignee: TC1, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/401,365

(22) Filed: Aug. 13, 2021

(65) Prior Publication Data

US 2021/0369123 A1    Dec. 2, 2021

Related U.S. Application Data

(60) Division of application No. 17/184,717, filed on Feb. 25, 2021, now Pat. No. 11,103,146, and a division of
(Continued)

(51) Int. Cl.
*A61B 5/00* (2006.01)
*A61B 5/0215* (2006.01)
(Continued)

(52) U.S. Cl.
CPC ........ *A61B 5/0215* (2013.01); *A61B 5/02055* (2013.01); *A61B 5/6882* (2013.01);
(Continued)

(58) Field of Classification Search
CPC . A61B 5/0031; A61B 5/0215; A61B 5/02158; A61B 5/02438; A61B 5/0265;
(Continued)

(56) References Cited

U.S. PATENT DOCUMENTS 2,769,863 A    11/1956   Graybill et al.
3,714,595 A     1/1973   Denenberg et al.
(Continued)

FOREIGN PATENT DOCUMENTS

CA    1158061 A    12/1983
CA    2840645 A1    1/2013
(Continued)

OTHER PUBLICATIONS

Extended European Search Report for Application No. 09755445 1.3 dated Nov. 4, 2013 (5 pages).
(Continued)

*Primary Examiner* — Paul D Kim
(74) *Attorney, Agent, or Firm* — The Small Patent Law Group LLC; Dean D. Small

(57) ABSTRACT

An implantable wireless sensor is provided for determining a pressure of a lumen in a body. The sensor comprises a sensor body comprising a plurality of substrates, at least a portion of the substrates comprising a first dielectric material. An LC resonant circuit is contained with the sensor body. A capacitance of the LC resonant circuit is configured to vary in response to changes in pressure in the lumen. A first anchoring element is coupled to a proximal end of the sensor body and a second anchoring element is coupled to a distal end of the sensor body. The first and second anchoring elements are configured to lodge the sensor body within the lumen. A second dielectric material, different than the first dielectric material, is provided over at least a portion of at least one of the plurality of substrates.

10 Claims, 23 Drawing Sheets

Related U.S. Application Data application No. 17/184,755, filed on Feb. 25, 2021, now Pat. No. 11,103,147, and a division of application No. 17/184,775, filed on Feb. 25, 2021, now Pat. No. 11,179,048, said application No. 17/184,717 is a division of application No. 16/194,103, filed on Nov. 16, 2018, now Pat. No. 11,033,192, which is a continuation of application No. 14/733,450, filed on Jun. 8, 2015, now Pat. No. 10,143,388, which is a continuation of application No. 12/612,070, filed on Nov. 4, 2009, now Pat. No. 9,078,563, which is a division of application No. 11/204,812, filed on Aug. 16, 2005, now Pat. No. 7,621,036, which is a continuation-in-part of application No. 11/157,375, filed on Jun. 21, 2005, now abandoned, said application No. 17/184,755 is a division of application No. 16/194,103, said application No. 17/184,775 is a division of application No. 16/194,103, which is a continuation of application No. 14/733,450, which is a continuation of application No. 12/612,070, which is a division of application No. 11/204,812, which is a continuation-in-part of application No. 11/157,375.

(51) Int. Cl.
- *H05K 3/32* (2006.01)
- *A61B 5/0205* (2006.01)
- *A61N 1/365* (2006.01)
- *A61B 5/024* (2006.01)

(52) U.S. Cl.
CPC ............ *H05K 3/32* (2013.01); *A61B 5/02427* (2013.01); *A61B 2562/0247* (2013.01); *A61B 2562/12* (2013.01); *A61N 1/36564* (2013.01); *Y10T 29/4913* (2015.01); *Y10T 29/49117* (2015.01)

(58) Field of Classification Search
CPC ......... A61B 5/029; A61B 5/063; A61B 5/145; A61B 5/14532; A61B 5/14865; A61B 5/14546; A61B 5/6867; H05K 3/32
See application file for complete search history.

(56) References Cited

U.S. PATENT DOCUMENTS

| | | |
|---|---|---|
| 3,867,950 A | 2/1975 | Fischell |
| 3,872,455 A | 3/1975 | Fuller et al. |
| 3,888,708 A | 6/1975 | Wise et al. |
| 3,942,382 A | 3/1976 | Hok |
| 3,943,915 A | 3/1976 | Severson |
| 3,958,558 A | 5/1976 | Dunphy et al. |
| 4,023,562 A | 5/1977 | Hynecek et al. |
| 4,026,276 A | 5/1977 | Chubbuck |
| 4,037,324 A | 7/1977 | Andreasen |
| 4,067,235 A | 1/1978 | Markland et al. |
| 4,127,110 A | 11/1978 | Bullara |
| 4,152,669 A | 5/1979 | Igarashi |
| 4,206,762 A | 6/1980 | Cosman |
| 4,207,903 A | 6/1980 | O'Neill |
| 4,237,900 A | 12/1980 | Schulman et al. |
| 4,354,506 A | 10/1982 | Sakaguchi et al. |
| 4,378,809 A | 4/1983 | Cosman |
| 4,385,636 A | 5/1983 | Cosman |
| 4,485,813 A | 12/1984 | Anderson et al. |
| 4,494,950 A | 1/1985 | Fischell |
| 4,511,858 A | 4/1985 | Charavit et al. |
| 4,521,684 A | 6/1985 | Gilby et al. |
| 4,531,526 A | 7/1985 | Genest |
| 4,567,459 A | 1/1986 | Folger et al. |
| 4,593,703 A | 6/1986 | Cosman |
| 4,596,563 A | 6/1986 | Pande |
| 4,644,420 A | 2/1987 | Buchan |
| 4,701,826 A | 10/1987 | Mikkor |
| 4,713,540 A | 12/1987 | Gilby et al. |
| 4,718,425 A | 1/1988 | Tanaka et al. |
| 4,796,641 A | 1/1989 | Mills et al. |
| 4,815,472 A | 3/1989 | Wise et al. |
| 4,846,191 A | 7/1989 | Brokway et al. |
| 4,881,410 A | 11/1989 | Wise et al. |
| 4,890,623 A | 1/1990 | Cook et al. |
| 4,899,752 A | 2/1990 | Cohen |
| 4,913,147 A | 4/1990 | Fahlstrom et al. |
| 4,934,369 A | 6/1990 | Maxwell |
| 4,953,387 A | 9/1990 | Johnson et al. |
| 4,966,034 A | 10/1990 | Bock et al. |
| 4,987,897 A | 1/1991 | Funke |
| 5,006,819 A | 4/1991 | Buchan et al. |
| 5,055,577 A | 4/1991 | Frenkel |
| 5,013,396 A | 5/1991 | Wise et al. |
| 5,046,497 A | 9/1991 | Millar |
| 5,055,838 A | 10/1991 | Wise et al. |
| 5,059,543 A | 10/1991 | Wise et al. |
| 5,108,420 A | 4/1992 | Marks |
| 5,113,868 A | 5/1992 | Wise et al. |
| 5,115,128 A | 5/1992 | Cook |
| 5,129,394 A | 7/1992 | Mehra |
| 5,165,289 A | 11/1992 | Tilmans |
| 5,181,423 A | 1/1993 | Phillips et al. |
| 5,192,314 A | 3/1993 | Daskalakis |
| 5,207,103 A | 5/1993 | Wise et al. |
| 5,257,630 A | 11/1993 | Broitman et al. |
| 5,262,127 A | 11/1993 | Wise et al. |
| 5,265,606 A | 11/1993 | Kujawski |
| 5,282,827 A | 2/1994 | Kensey et al. |
| 5,296,255 A | 3/1994 | Gland et al. |
| 5,334,952 A | 8/1994 | Maddy et al. |
| 5,343,064 A | 8/1994 | Spangler et al. |
| 5,353,800 A | 10/1994 | Pohndorf et al. |
| 5,373,582 A | 12/1994 | Harrison et al. |
| 5,377,524 A | 1/1995 | Wise et al. |
| 5,411,551 A | 5/1995 | Winston et al. |
| 5,417,235 A | 5/1995 | Wise et al. |
| 5,431,171 A | 7/1995 | Harrison et al. |
| 5,440,300 A | 8/1995 | Spillman, Jr. |
| 5,454,270 A | 10/1995 | Brown et al. |
| 5,487,760 A | 1/1996 | Villafana |
| 5,497,099 A | 3/1996 | Walton |
| 5,510,276 A | 4/1996 | Diem et al. |
| 5,515,041 A | 5/1996 | Spillman, Jr. |
| 5,535,752 A | 7/1996 | Halperin et al. |
| 5,538,005 A | 7/1996 | Harrison et al. |
| 5,551,427 A | 9/1996 | Altman |
| 5,564,434 A | 10/1996 | Halperin et al. |
| 5,566,676 A | 10/1996 | Rosenfeldt et al. |
| 5,581,248 A | 12/1996 | Spillman, Jr. et al. |
| 5,593,430 A | 1/1997 | Renger |
| 5,600,245 A | 2/1997 | Yamamoto et al. |
| 5,626,630 A | 5/1997 | Markowitz et al. |
| 5,686,841 A | 11/1997 | Stolarczyk et al. |
| 5,690,674 A | 11/1997 | Diaz |
| 5,695,155 A | 12/1997 | Macdonald et al. |
| 5,702,427 A | 12/1997 | Exker et al. |
| 5,703,576 A | 12/1997 | Spillman, Jr. et al. |
| 5,713,917 A | 2/1998 | Leonhardt et al. |
| 5,722,414 A | 3/1998 | Archibald et al. |
| 5,723,791 A | 3/1998 | Koch et al. |
| 5,743,267 A | 4/1998 | Nikolic et al. |
| 5,796,827 A | 8/1998 | Coppersmith et al. |
| 5,807,265 A | 9/1998 | Itoigawa et al. |
| 5,836,886 A | 11/1998 | Itoigawa et al. |
| 5,840,148 A | 11/1998 | Campbell et al. |
| 5,860,938 A | 1/1999 | Lafontaine et al. |
| 5,872,520 A | 2/1999 | Seifert et al. |
| 5,896,113 A | 4/1999 | O'Neill, Jr. |
| 5,899,927 A | 5/1999 | Ecker et al. |
| 5,920,233 A | 7/1999 | Denny |
| 5,925,076 A | 7/1999 | Inoue |
| 5,935,084 A | 8/1999 | Southworth |
| 5,942,991 A | 8/1999 | Gaudreau et al. |
| 5,967,986 A | 10/1999 | Cimochowski et al. |

(56) References Cited

U.S. PATENT DOCUMENTS

| | | |
|---|---|---|
| 5,992,769 A | 11/1999 | Wise et al. |
| 5,994,638 A | 11/1999 | Edelson |
| 6,015,386 A | 1/2000 | Kensey et al. |
| 6,015,387 A | 1/2000 | Schwartz et al. |
| 6,019,729 A | 2/2000 | Itoigawa et al. |
| 6,024,704 A | 2/2000 | Meador et al. |
| 6,025,725 A | 2/2000 | Gershenfeld et al. |
| 6,030,413 A | 2/2000 | Lazarus |
| 6,033,366 A | 3/2000 | Brockway et al. |
| 6,053,873 A | 4/2000 | Govari et al. |
| 6,076,016 A | 6/2000 | Feierbach |
| 6,109,113 A | 8/2000 | Chavan et al. |
| 6,111,520 A | 8/2000 | Allen et al. |
| 6,113,553 A | 9/2000 | Chubbuck |
| 6,126,675 A | 10/2000 | Shchervinsky et al. |
| 6,134,461 A | 10/2000 | Say et al. |
| 6,140,144 A | 10/2000 | Najafi et al. |
| 6,140,740 A | 10/2000 | Porat et al. |
| 6,159,156 A | 12/2000 | Van Bockel |
| 6,174,322 B1 | 1/2001 | Schneidt |
| 6,190,400 B1 | 2/2001 | Van De Moer et al. |
| 6,198,965 B1 | 3/2001 | Penner et al. |
| 6,200,270 B1 | 3/2001 | Biehl et al. |
| 6,201,980 B1 | 3/2001 | Darrow et al. |
| 6,206,835 B1 | 3/2001 | Spillman, Jr. et al. |
| 6,232,150 B1 | 5/2001 | Lin et al. |
| 6,237,398 B1 | 5/2001 | Porat et al. |
| 6,239,724 B1 | 5/2001 | Doron et al. |
| 6,259,328 B1 | 7/2001 | Wesolowski |
| 6,277,078 B1 | 8/2001 | Porat et al. |
| 6,278,379 B1 | 8/2001 | Allen et al. |
| 6,287,253 B1 | 9/2001 | Ortega et al. |
| 6,287,256 B1 | 9/2001 | Park et al. |
| 6,309,350 B1 | 10/2001 | VanTassel et al. |
| 6,331,163 B1 | 12/2001 | Kaplan |
| 6,338,284 B1 | 1/2002 | Najafi et al. |
| 6,359,444 B1 | 3/2002 | Grimes |
| 6,373,264 B1 | 4/2002 | Matsumoto et al. |
| 6,409,674 B1 | 6/2002 | Brockway et al. |
| 6,416,474 B1 | 7/2002 | Penner et al. |
| 6,442,413 B1 | 8/2002 | Silver |
| 6,447,449 B1 | 9/2002 | Fleischman et al. |
| 6,454,720 B1 | 9/2002 | Clerc et al. |
| 6,459,253 B1 | 10/2002 | Krussell |
| 6,471,656 B1 | 10/2002 | Shalman et al. |
| 6,477,901 B1 | 11/2002 | Tadigadapa et al. |
| 6,499,354 B1 | 12/2002 | Najafi et al. |
| 6,570,457 B2 | 5/2003 | Fischer |
| 6,592,608 B2 | 7/2003 | Fisher et al. |
| 6,636,769 B2 | 10/2003 | Govari et al. |
| 6,645,143 B2 | 11/2003 | VanTassel et al. |
| 6,647,778 B2 | 11/2003 | Sparks |
| 6,658,300 B2 | 12/2003 | Govari et al. |
| 6,666,826 B2 | 12/2003 | Salo et al. |
| 6,667,725 B1 | 12/2003 | Simons et al. |
| 6,680,654 B2 | 1/2004 | Fischer et al. |
| 6,682,490 B2 | 1/2004 | Roy et al. |
| 6,713,828 B1 | 3/2004 | Chavan et al. |
| 6,743,183 B1 | 6/2004 | Thornton |
| 6,749,622 B2 | 6/2004 | McGuckin, Jr. et al. |
| 6,764,446 B2 | 7/2004 | Wolinsky et al. |
| 6,765,493 B2 | 7/2004 | Lonsdale et al. |
| 6,779,406 B1 | 8/2004 | Kuznia et al. |
| 6,783,499 B2 | 8/2004 | Schwartz |
| 6,805,667 B2 | 10/2004 | Christopherson et al. |
| 6,824,521 B2 | 11/2004 | Rich et al. |
| 6,838,640 B2 | 1/2005 | Wise et al. |
| 6,844,213 B2 | 1/2005 | Sparks |
| 6,855,115 B2 | 2/2005 | Fonseca et al. |
| 6,890,300 B2 | 5/2005 | Lloyd et al. |
| 6,893,885 B2 | 5/2005 | Lemmerhirt et al. |
| 6,916,310 B2 | 7/2005 | Sommerich |
| 6,919,240 B2 | 7/2005 | Uzawa et al. |
| 6,923,625 B2 | 8/2005 | Sparks |
| 6,923,769 B2 | 8/2005 | Nishii et al. |
| 6,926,670 B2 | 8/2005 | Rich et al. |
| 6,932,114 B2 | 8/2005 | Sparks |
| 6,935,010 B2 | 8/2005 | Tadigadapa et al. |
| 6,939,299 B1 | 9/2005 | Petersen et al. |
| 6,945,939 B2 | 9/2005 | Turcott |
| 6,959,608 B2 | 11/2005 | Bly et al. |
| 6,968,743 B2 | 11/2005 | Rich et al. |
| 6,981,958 B1 | 1/2006 | Gharib et al. |
| 7,001,398 B2 | 2/2006 | Carley et al. |
| 7,004,015 B2 | 2/2006 | Chang-Chien et al. |
| 7,013,734 B2 | 3/2006 | Zdeblick et al. |
| 7,025,727 B2 | 4/2006 | Brockway et al. |
| 7,028,550 B2 | 4/2006 | Zdeblick et al. |
| 7,048,756 B2 | 5/2006 | Eggers et al. |
| 7,059,176 B2 | 6/2006 | Sparks |
| 7,059,195 B1 | 6/2006 | Liu et al. |
| 7,066,031 B2 | 6/2006 | Zdeblick et al. |
| 7,073,387 B2 | 7/2006 | Zdeblick et al. |
| 7,081,125 B2 | 7/2006 | Edwards et al. |
| 7,134,341 B2 | 11/2006 | Girmonsky et al. |
| 7,137,953 B2 | 11/2006 | Eigler et al. |
| 7,146,861 B1 | 12/2006 | Cook et al. |
| 7,147,604 B1 | 12/2006 | Allen et al. |
| 7,149,587 B2 | 12/2006 | Wardle et al. |
| 7,162,926 B1 | 1/2007 | Guziak et al. |
| 7,174,212 B1 | 2/2007 | Klehn et al. |
| 7,192,001 B2 | 3/2007 | Wise et al. |
| 7,198,603 B2 | 4/2007 | Penner et al. |
| 7,211,048 B1 | 5/2007 | Najafi et al. |
| 7,228,735 B2 | 6/2007 | Sparks et al. |
| 7,245,117 B1 | 7/2007 | Joy et al. |
| 7,273,457 B2 | 9/2007 | Penner |
| 7,284,442 B2 | 10/2007 | Fleischman et al. |
| 7,290,454 B2 | 11/2007 | Liu |
| 7,401,521 B2 | 7/2008 | Bellini et al. |
| 7,425,200 B2 | 9/2008 | Brockway et al. |
| 7,432,723 B2 | 10/2008 | Ellis et al. |
| 7,439,723 B2 | 10/2008 | Allen et al. |
| 7,466,120 B2 | 12/2008 | Miller et al. |
| 7,475,792 B2 | 1/2009 | Hansen |
| 7,483,805 B2 | 1/2009 | Sparks et al. |
| 7,492,144 B2 | 2/2009 | Powers et al. |
| 7,498,799 B2 | 3/2009 | Allen et al. |
| 7,550,978 B2 | 6/2009 | Joy et al. |
| 7,574,792 B2 | 8/2009 | O'Brien et al. |
| 7,641,619 B2 | 1/2010 | Penner |
| 7,647,831 B2 | 1/2010 | Corcoran et al. |
| 7,647,836 B2 | 1/2010 | O'Brien et al. |
| 7,679,355 B2 | 3/2010 | Allen et al. |
| 7,686,762 B1 | 3/2010 | Najafi et al. |
| 7,710,103 B2 | 5/2010 | Powers et al. |
| 7,763,487 B2 | 7/2010 | Villa et al. |
| 7,839,153 B2 | 11/2010 | Joy et al. |
| 7,932,732 B2 | 4/2011 | Ellis et al. |
| 7,936,174 B2 | 5/2011 | Ellis et al. |
| 7,966,886 B2 | 6/2011 | Corcoran |
| 8,021,307 B2 | 9/2011 | White et al. |
| 8,025,625 B2 | 9/2011 | Allen |
| 8,118,749 B2 | 2/2012 | White et al. |
| 8,132,465 B1 | 3/2012 | Doelle et al. |
| 8,154,389 B2 | 4/2012 | Rowland et al. |
| 8,237,451 B2 | 8/2012 | Joy et al. |
| 8,353,841 B2 | 1/2013 | White et al. |
| 8,355,777 B2 | 1/2013 | White et al. |
| 8,360,984 B2 | 1/2013 | Yadav et al. |
| 8,432,265 B2 | 4/2013 | Rowland et al. |
| 8,493,187 B2 | 7/2013 | Rowland et al. |
| 9,265,428 B2 | 2/2016 | O'Brien et al. |
| 9,305,456 B2 | 4/2016 | Rowland et al. |
| 10,003,862 B2 | 6/2018 | Rowland et al. |
| 10,603,224 B2 | 3/2020 | Prokopuk |
| 10,638,955 B2 | 5/2020 | Rowland et al. |
| 2002/0045921 A1 | 4/2002 | Wolinsky et al. |
| 2002/0072656 A1 | 6/2002 | Vantassel et al. |
| 2002/0115920 A1 | 8/2002 | Rich et al. |
| 2002/0138009 A1 | 9/2002 | Brockway et al. |
| 2002/0151816 A1 | 10/2002 | Rich et al. |
| 2002/0177782 A1 | 11/2002 | Penner |
| 2002/0188207 A1 | 12/2002 | Richter |

(56) References Cited

U.S. PATENT DOCUMENTS

| | | | |
|---|---|---|---|
| 2003/0062957 A1 | 4/2003 | Terashima et al. |
| 2003/0125790 A1 | 7/2003 | Fastovsky et al. |
| 2003/0136417 A1 | 7/2003 | Fonseca et al. |
| 2003/0139677 A1 | 7/2003 | Fonseca et al. |
| 2003/0139771 A1 | 7/2003 | Fisher et al. |
| 2003/0158584 A1 | 8/2003 | Cates et al. |
| 2003/0191496 A1 | 10/2003 | Edwards et al. |
| 2004/0102806 A1 | 5/2004 | Broome et al. |
| 2004/0158138 A1 | 8/2004 | Kilcoyne et al. |
| 2004/0176672 A1 | 9/2004 | Silver et al. |
| 2004/0220637 A1 | 11/2004 | Zdeblick et al. |
| 2004/0239504 A1 | 12/2004 | Kalinin et al. |
| 2004/0255643 A1 | 12/2004 | Wise et al. |
| 2004/0260164 A1 | 12/2004 | Kilcoyne et al. |
| 2005/0013685 A1 | 1/2005 | Ricketts et al. |
| 2005/0015014 A1 | 1/2005 | Fonseca et al. |
| 2005/0043601 A1 | 2/2005 | Kilcoyne et al. |
| 2005/0049634 A1 | 3/2005 | Chopra |
| 2005/0075697 A1 | 4/2005 | Olson et al. |
| 2005/0080346 A1 | 4/2005 | Gianchandani et al. |
| 2005/0085703 A1 | 4/2005 | Behm |
| 2005/0090719 A1 | 4/2005 | Scheiner et al. |
| 2005/0103114 A1 | 5/2005 | Bly et al. |
| 2005/0124896 A1 | 6/2005 | Richter et al. |
| 2005/0154321 A1 | 7/2005 | Wolinsky et al. |
| 2005/0160825 A1 | 7/2005 | Zdeblick et al. |
| 2005/0160827 A1 | 7/2005 | Zdeblick et al. |
| 2005/0187482 A1 | 8/2005 | O'Brien et al. |
| 2005/0228308 A1 | 10/2005 | Iddan et al. |
| 2005/0288596 A1 | 12/2005 | Eigler et al. |
| 2005/0288604 A1 | 12/2005 | Eigler et al. |
| 2005/0288722 A1 | 12/2005 | Eigler et al. |
| 2006/0047205 A1 | 3/2006 | Ludomirsky et al. |
| 2006/0052821 A1 | 3/2006 | Abbott et al. |
| 2006/0064133 A1 | 3/2006 | Von Arx et al. |
| 2006/0064134 A1 | 3/2006 | Mazar et al. |
| 2006/0064142 A1 | 3/2006 | Chavan et al. |
| 2006/0064143 A1 | 3/2006 | Von Arx et al. |
| 2006/0085039 A1 | 4/2006 | Hastings et al. |
| 2006/0109188 A1 | 5/2006 | Ikeda et al. |
| 2006/0122522 A1 | 6/2006 | Chavan et al. |
| 2006/0129050 A1 | 6/2006 | Martinson et al. |
| 2006/0137461 A1 | 6/2006 | Bellini et al. |
| 2006/0161171 A1 | 7/2006 | Schwartz |
| 2006/0174712 A1 | 8/2006 | O'Brien et al. |
| 2006/0177956 A1 | 8/2006 | O'Brien et al. |
| 2006/0178583 A1 | 8/2006 | Montegrande et al. |
| 2006/0178695 A1 | 8/2006 | Decant, Jr. et al. |
| 2006/0196277 A1 | 9/2006 | Allen et al. |
| 2006/0206146 A1 | 9/2006 | Tenerz |
| 2006/0212047 A1 | 9/2006 | Abbott et al. |
| 2006/0217762 A1 | 9/2006 | Maahs et al. |
| 2006/0217763 A1 | 9/2006 | Abbott et al. |
| 2006/0217764 A1 | 9/2006 | Abbott et al. |
| 2006/0229488 A1 | 10/2006 | Ayre et al. |
| 2006/0235310 A1 | 10/2006 | O'Brien et al. |
| 2006/0241354 A1 | 10/2006 | Allen |
| 2006/0244465 A1 | 11/2006 | Kroh et al. |
| 2006/0271078 A1 | 11/2006 | Modesitt |
| 2006/0287602 A1 | 12/2006 | O'Brien et al. |
| 2006/0287700 A1* | 12/2006 | White .................. A61B 5/076 607/127 |
| 2007/0007240 A1 | 1/2007 | Wise et al. |
| 2007/0028698 A1 | 2/2007 | Guziak et al. |
| 2007/0032734 A1 | 2/2007 | Najaf et al. |
| 2007/0049980 A1 | 3/2007 | Zielinski et al. |
| 2007/0049984 A1 | 3/2007 | Osypka |
| 2007/0060959 A1 | 3/2007 | Salo et al. |
| 2007/0073351 A1 | 3/2007 | Zielinski et al. |
| 2007/0088388 A1 | 4/2007 | Opolski et al. |
| 2007/0096715 A1 | 5/2007 | Joy et al. |
| 2007/0100215 A1 | 5/2007 | Powers et al. |
| 2007/0106246 A1 | 5/2007 | Modesitt |
| 2007/0106328 A1 | 5/2007 | Wardle et al. |
| 2007/0106333 A1 | 5/2007 | Fernandez |
| 2007/0112358 A1 | 5/2007 | Abbott et al. |
| 2007/0118038 A1 | 5/2007 | Bodecker et al. |
| 2007/0118039 A1 | 5/2007 | Bodecker et al. |
| 2007/0144494 A1 | 6/2007 | Mori et al. |
| 2007/0149880 A1 | 6/2007 | Willis |
| 2007/0160748 A1 | 7/2007 | Schugt et al. |
| 2007/0163355 A1 | 7/2007 | Nassar et al. |
| 2007/0199385 A1 | 8/2007 | O'Brien et al. |
| 2007/0208390 A1 | 9/2007 | Von Arx et al. |
| 2007/0210786 A1 | 9/2007 | Mien et al. |
| 2007/0267708 A1 | 11/2007 | Coucimault |
| 2008/0269573 A1 | 10/2008 | Najaf et al. |
| 2008/0269829 A1 | 10/2008 | Li et al. |
| 2008/0281212 A1 | 11/2008 | Nunez et al. |
| 2009/0030291 A1 | 1/2009 | O'Brien et al. |
| 2009/0115396 A1 | 5/2009 | Allen et al. |
| 2009/0221885 A1 | 9/2009 | Hall et al. |
| 2009/0224773 A1 | 9/2009 | Joy et al. |
| 2009/0224837 A1 | 9/2009 | Joy et al. |
| 2009/0278553 A1 | 11/2009 | Kroh et al. |
| 2010/0022896 A1 | 1/2010 | Yadav et al. |
| 2010/0026318 A1 | 2/2010 | Kroh et al. |
| 2010/0161004 A1 | 6/2010 | Najaf et al. |
| 2010/0308974 A1 | 12/2010 | Rowland et al. |
| 2011/0046452 A1 | 2/2011 | Najaf et al. |
| 2011/0063088 A1 | 3/2011 | Stevenson et al. |
| 2011/0156178 A1 | 6/2011 | Zuniga-Ortiz et al. |
| 2011/0224595 A1 | 9/2011 | Pedersen et al. |
| 2012/0286934 A1 | 11/2012 | Rowland et al. |
| 2014/0028467 A1 | 1/2014 | Nagy et al. |
| 2014/0155710 A1 | 6/2014 | Rowland et al. |
| 2014/0306807 A1 | 10/2014 | Rowland et al. |
| 2014/0330143 A1 | 11/2014 | Kroh et al. |
| 2016/0029956 A1 | 2/2016 | Rowland et al. |
| 2017/0181646 A1 | 6/2017 | Hayes et al. |

FOREIGN PATENT DOCUMENTS

| | | |
|---|---|---|
| CN | 1701464 A | 11/2005 |
| CN | 1826686 A | 8/2006 |
| CN | 101116322 A | 1/2008 |
| CN | 101128957 A | 2/2008 |
| CN | 101278439 A | 10/2008 |
| CN | 101427923 A | 5/2009 |
| DE | 19644858 A1 | 5/1997 |
| EP | 1337035 B1 | 11/1993 |
| EP | 0646365 B1 | 1/2004 |
| HK | 1147906 A | 8/2011 |
| JP | 2000005136 A | 1/2000 |
| JP | 2000517073 A | 12/2000 |
| JP | 2002515278 A | 5/2002 |
| JP | 2003144417 A | 5/2003 |
| JP | 2005284511 A | 10/2005 |
| JP | 2006512112 A | 4/2006 |
| JP | 2006309582 A | 11/2006 |
| JP | 2007210547 A | 8/2007 |
| JP | 2007256287 A | 10/2007 |
| JP | 2008022935 A | 2/2008 |
| JP | 2008532590 A | 8/2008 |
| JP | 2010538254 A | 12/2010 |
| WO | 8303348 A | 10/1983 |
| WO | 9006723 A | 6/1990 |
| WO | 9533517 A | 12/1995 |
| WO | 9709926 A | 3/1997 |
| WO | 9732519 A | 9/1997 |
| WO | 9733513 A | 9/1997 |
| WO | 9732518 A | 12/1997 |
| WO | 9934731 A | 7/1999 |
| WO | 0016686 A | 3/2000 |
| WO | 0100089 A1 | 1/2001 |
| WO | 0187137 A2 | 11/2001 |
| WO | 0197908 A1 | 12/2001 |
| WO | 03061504 A | 7/2003 |
| WO | 2004045407 A1 | 6/2004 |
| WO | 2005027998 A2 | 3/2005 |
| WO | 2005107583 A3 | 11/2005 |
| WO | 2006049796 A2 | 5/2006 |
| WO | 2006070278 A1 | 7/2006 |
| WO | 2006096582 A1 | 9/2006 |

(56) References Cited

FOREIGN PATENT DOCUMENTS

| WO | 2006130488 A3 | 12/2006 |
|---|---|---|
| WO | 2007030489 A1 | 3/2007 |
| WO | 2008115456 A1 | 9/2008 |
| WO | 2009146089 A2 | 12/2009 |
| WO | 2010117356 A1 | 10/2010 |
| WO | 2010117597 A1 | 10/2010 |
| WO | 2012015955 A1 | 2/2012 |
| WO | 2013033506 A1 | 3/2013 |

OTHER PUBLICATIONS

Patent Cooperation Treaty (PCT), International Search Report and Written Opinion for Application PCT/US12/44998, dated Sep. 25, 2012, 9 pgs., International Searching Authority, US.
A. Magalski, P. Adamson, F. Gadler, M. Boehm, D. Steinhaus, D. Reynolds,K. Vlach, C. Linde, B. Cremers, B. Sparks, T. Bennet; "Continuous Ambulatory Right Heart Presure Measurements with an Implantable Hemodynamic Monitor: A Multicenter, 12-Month Follow-Up Study of Patients with Chronic Heart Failure"; Journal of Cardiac failure, vol. 8, Apr. 2002, pp. 63-70.
B. Sonesson, N. Dias, M. Malina, P. Olofsson, D. Griffin, B. Lindblad, K. Ivancev; "Intra-Aneurysm Pressure Measurements in Successfully Excluded Abdominal Aortic Aneurysm After Endovascular Repair"; Journal of Vascular Surgery, vol. 37, No. 4, Apr. 2003, pp. 733-738.
C.S. Skillern, S.L. Stevens, K.T. Piercy, R.L. Donnell, M.B. Freeman, M.H. Goldman; "Endotension in an Experimental Aneurysm Model"; Journal of Vascular Surgery, vol. 36, No. 4, Oct. 2002, pp. 814-817.
Communication pursuant to Article 94(3) EPC from the European Patent Office; Application No. 10 762 085.8-1660; dated Sep. 17, 2015.
Communication pursuant to Article 94(3) EPC from the European Patent Office; Application No. 10 762 085.8-1660; dated Jan. 26, 2015.
European Patent Office; Extended European Search Report for European Pat. App. 17000257.0 ; dated Jun. 4, 2017.
Extended European Search Report for Application 12804636.4 PCT/US2012044998, dated Jan. 20, 2015, 6pgs., European Patent Office, Germany.
Extended European Search Report for Application 14806873.7 PCT/US2014030661, dated May 20, 2016, 7 pp., European Patent Office, Germany.
Extended European Search Report, Endotronix, Inc., Application No. 10762085.8-2319/2417590, dated Jan. 4, 2013.
G.D. Treharne, I.M. Loftus, M.M. Thompson, N. Leonard, J. Smith, G. Fishwick, PRF Bell; "Quality Control During Endovascular Aneurysm Repair: Monitoring Aneurysmal Sac Pressure and Superficial Femoral Artery Flow Velocity"; J. Endovasc Surg. 1999, 6, pp. 239-245.
GWH Schurink, NJM Arts, J Wild, J.M Van Baalen, Tam Chutner, LJ Schultze Kool, JH Van Bockel; "Endoleakage After Stent-Graft Treatment of Abdominal Aneurysm: Implications on Pressure and Imaging—An In Vitro Study"; Journal of Vascular Surgery, vol. 28, No. 2, pp. 234-241, Aug. 1998.
GWH Schurink, NJM Arts, J.M Van Baalen, L.J Schultze Kool, JH Van Bockel; "Experimental Study of the Influence of Endoleakage Size on Pressure in the Aneurysm Sac and the Consequences of Thrombosis"; British Journal of Surgery 2002, 87, pp. 71-78.
International Preliminary Report on Patentability, Endotronix, Inc., PCT/US2012/034979, dated Oct. 29, 2013.
International Preliminary Report on Patentability, Nunez, Anthony, I. et al., PCT/US2008/003475, dated Sep. 24, 2009.
International Search Report and the Written Opinion of the International Searching Authority, Endotronix, Inc., PCT/US2009/39730, dated Jun. 30, 2009.
International Search Report and the Written Opinion of the International Searching Authority, Endotronix, Inc., PCT/US2010/27951, dated Aug. 25, 2010.
International Search Report and the Written Opinion of the International Searching Authority, Endotronix, Inc., PCT/US2012/34979, dated Nov. 2, 2012.
International Search Report and Written Opinion of the International Searching Authority for PCT/US2017/042702 dated Apr. 3, 2018, 17 pages.
J.C. Parodi, R. Berguer, L.M. Ferreira, R. Lamura, M.L. Schererhorn; "Intra-eneurysmal Pressure After Incomplete Endovascular Exclusion"; Journal of Vascular Surgery, vol. 24, No. 5, Nov. 2001, pp. 909-914.
J.T. Farrar, C. Berkley, V.K. Zworykin; "Telemetering of Intraenteric pressure In man by an Externally Energized Wireless Capsule"; Science, New Series, vol. 131, Issue 3416 (Jun. 17, 1960), 1814.
K.F. Adams, Jr.; "Guiding Heart Failure Care by Invasive Hemodynamic Measurements: Possible or Useful?"; Journal of cardiac failure, vol. 8, No. 2, Apr. 2002, pp. 71-73.
M. Gawenda, J. Heckenkamp, M. Zaehringer, J. Brunkwall; "Intra-Aneurysm Sac Pressure—The Holy Gail of Endoluminal Grafting of AAA"; Eur J Vasc Endovasc Surg. vol. 24, Aug. 2002, pp. 139-145.
M.L. Manwaring, V.D. Malbasa, K.L. Manwaring: "Remote Monitoring of Intracernial Pressure"; Institute of Concology; Annals of the Academy of Studencia Apr. 2001; pp. 77-80.
Office Action from the USPTO; U.S. Appl. No. 13/860,851; dated Oct. 5, 2015.
Office Action—mailing No. 017790 from the Japanese Patent Office; (English Translation); Patent Application No. 2012-504690; dated Jan. 21, 2014.
Office Action—mailing No. 503764 from the Japanese Patent Office; (English Translation); Patent Application No. 2012-504690; dated Nov. 4, 2015.
Office Action—mailing No. 612064 from the Japanese Patent Office; (English Translation); Patent Application No. 2012-504690; dated Nov. 25, 2014.
P.L. Harris, S. Dimitri; "Predicting failure of endovascular Aneurysm repair"; Eur J Vasc Endovasc Surg, vol. 17, Jan. 1999; pp. 1-2.
R. Shabetai; "Monitoring Heart Failure Hemodynamics with an Implanted Device: Its Potential to Improve Outcome"; Journal of the American College of Cardiology; vol. 41, No. 4, Feb. 19, 2003; pp. 572-573.
R.A. Baum, J.P. Carpenter, C. Cope, M.A. Golden, O.C. Velazquez, D.G. Neschis, M.E. Mitchell, C.F. Barker, R.M. Fairman; "Aneurysm Sac Pressure measurements After Endovascular Repair of Abdominal Aortic Aneurysms"; Journal of Vascular Surgery, vol. 33, No. 1, Jan. 2001, pp. 32-41.
T. Akin, B. Ziaie, K. Najafi; "RF Telemetry Powering and Controlling of Hermetically Sealed Integrated Sensors and Actuators"; Center for Integrated Sensors and Circuits; Department of Electrical Engineering and Computer Science; University of Michigan; Ann Arbor, Michigan 48109-2122; pp. 145-148, 1990.
T. Chuter, K. Ivancev, M. Malina, T. Resch, J. Brunkwall, B. Lindblad, B. Risberg; "Endovascular and Surgical techniques"; Eur J. Vasc Endovasc Surg vol. 13, Jan. 1997, pp. 85-87.
Australian Patent Examination Report No. 1; Endotronix, Inc.; Application No. 2010235020; dated Aug. 18, 2014.
Collins, Carter, Miniature Passive Pressure Transensor for Implanting in the Eye, Transactions on Bio-Medical Engineering, vol. BME-14, No. 2, pp. 74-83, Apr. 1967.
International Search Report and the Written Opinion of the International Searching Authority, Nunez, Anthony I, PCT/US2008/03475, dated Aug. 4, 2008.
International Search Report dated Jul. 28, 2006 in PCT Patent Application No. PCT/US2006/007790.
Nagumo, J., Uchiyama, A., Kimoto, S., Watanuki, T., Hori, M., Suma, K, Ouchi, A., Kumano, M., and Watanabe, H., Echo Capsule for Medical Use (A Batteryless Endoradiosonde), IRE Transaction on Bio-Medical Electronics, pp. 195-199, 1962.
Patent Cooperation Treaty (PCT), International Search Report and Written Opinion for Application PCT/US/14/30661, dated Sep. 17, 2015, 8 pp., Interational Searching Authority, US.

(56) References Cited

OTHER PUBLICATIONS

Extended European Search Report for related European Patent Application No. 21169944.2 dated Aug. 27, 2021 (13 pages).

* cited by examiner

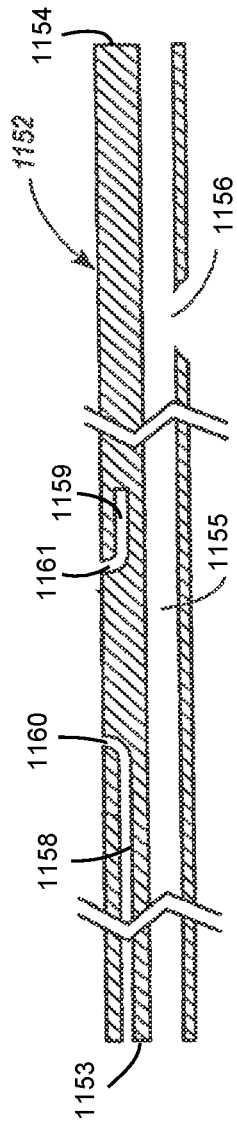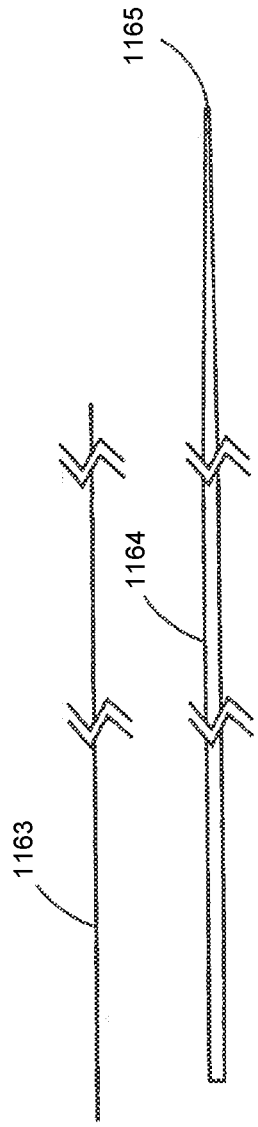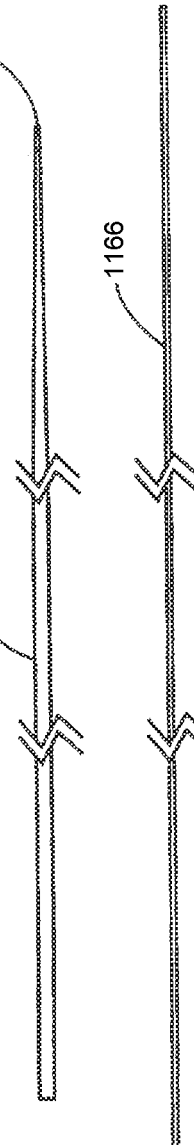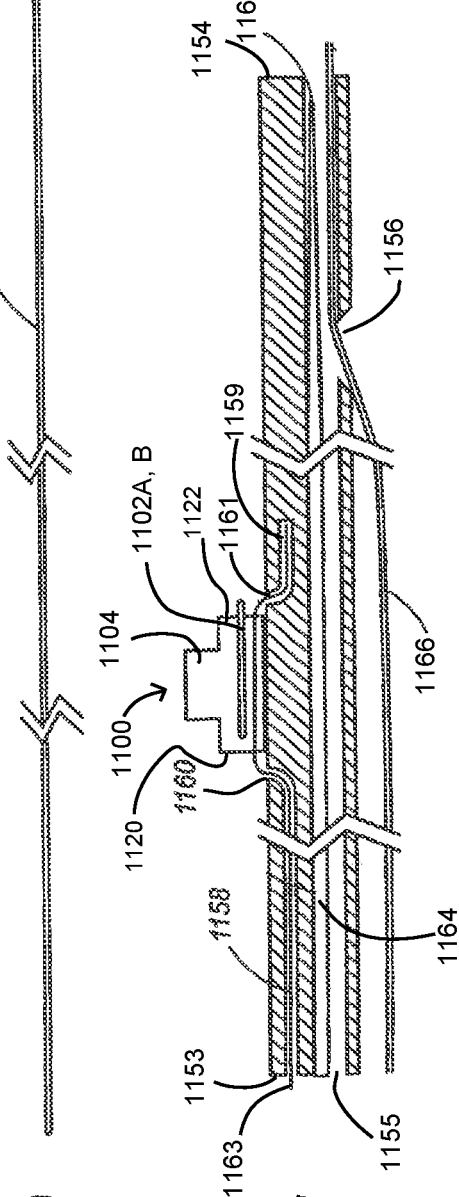
Fig. 47
Fig. 48
Fig. 49
Fig. 50
Fig. 51

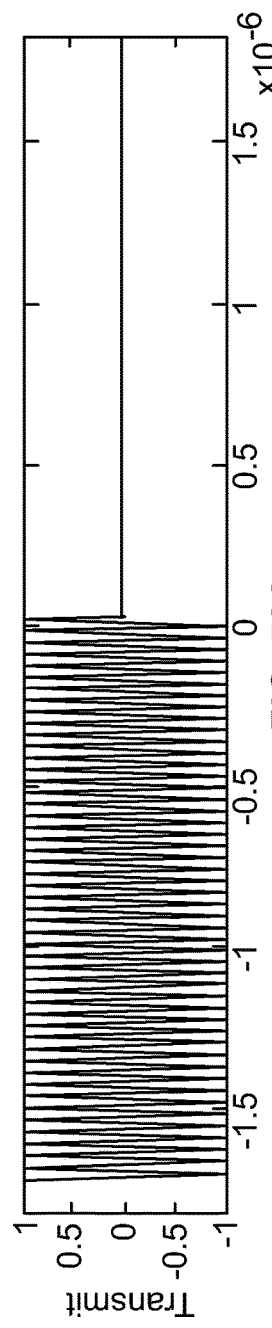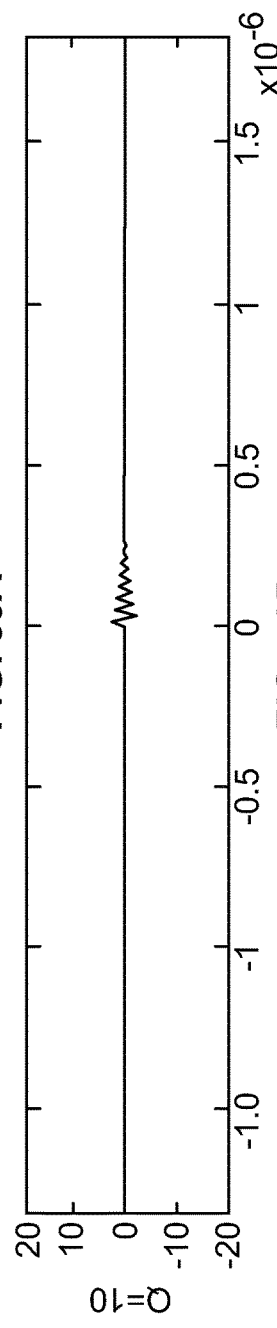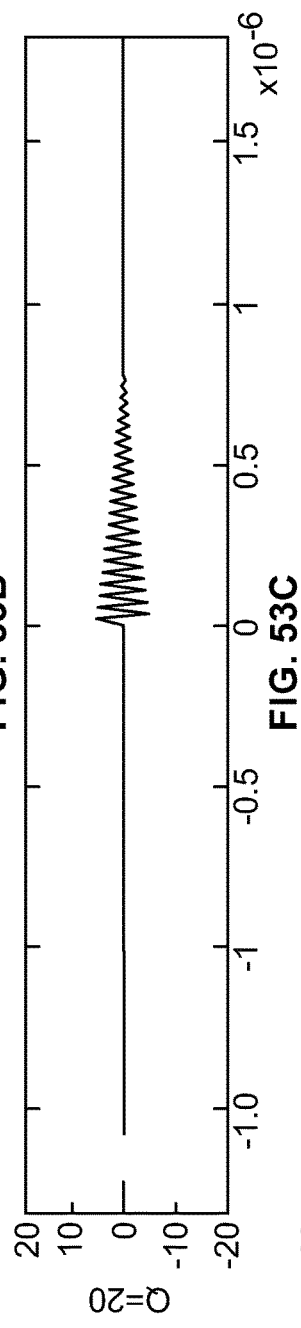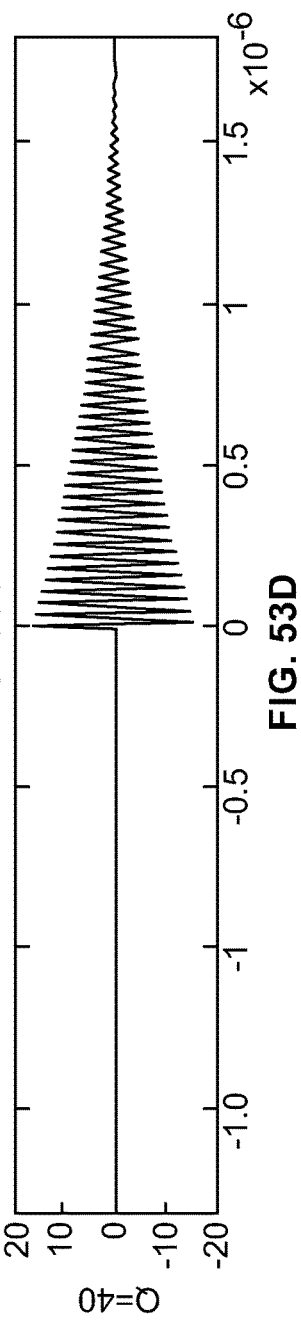

IMPLANTABLE WIRELESS PRESSURE SENSOR

CROSS-REFERENCE TO RELATED APPLICATION

The present application is a divisional application of U.S. application Ser. No. 17/184,717, filed 25 Feb. 2021 entitled "Wireless Sensor for Measuring Pressure" (now U.S. Pat. No. 11,103,146). The present application is a divisional application of U.S. application Ser. No. 17/184,755, filed 25 Feb. 2021 entitled "Method and System for Determining a Lumen Pressure" (now U.S. Pat. No. 11,103,147). The present application is a divisional application of U.S. application Ser. No. 17/184,775, filed 25 Feb. 2021 entitled "System and Method for Developing an Implant Assembly".

The '717, '755 and '775 applications are divisional applications of U.S. application Ser. No. 16/194,103, filed 16 Nov. 2018 entitled "Wireless Sensor for Measuring Pressure" (now U.S. Pat. No. 11,033,192), which is a continuation application of U.S. application Ser. No. 14/733,450, filed 8 Jun. 2015 entitled "Method of Manufacturing Implantable Wireless Sensor for In Vivo Pressure Measurement" (now U.S. Pat. No. 10,143,388), which is a continuation of U.S. application Ser. No. 12/612,070, filed 4 Nov. 2009 entitled "Method of Manufacturing Implantable Wireless Sensor for In Vivo Pressure Measurement" (now U.S. Pat. No. 9,078,563), which a divisional of U.S. application Ser. No. 11/204,812 filed 16 Aug. 2005 entitled "Method of Manufacturing Implantable Wireless Sensor for In Vivo Pressure Measurement" (now U.S. Pat. No. 7,621,036), which is a continuation-in-part of U.S. application Ser. No. 11/157,375, filed 21 Jun. 2005, entitled "Implantable Wireless Sensor for In Vivo Pressure Measurement" (now abandoned) the complete subject matter of each are expressly incorporated herein by reference in their entirety.

TECHNICAL FIELD

Embodiments herein relate to implantable sensors and methods of manufacturing implanted sensors for wirelessly sensing pressure, temperature and other physical properties within the human body. More particularly, embodiments herein concerns a method of manufacturing a wireless, un-powered, micromachined pressure sensor that can be delivered using catheter-based endovascular or surgical techniques to a location within an organ or vessel. Embodiments are further directed in general to communicating with a wireless sensor, and in particular to communicating with a wireless sensor implanted within the body to measure a physical condition.

BACKGROUND

The measurement of blood pressure within the human heart and its vasculature provides critical information regarding the organ's function. Many methods and techniques have been developed to give physicians the ability to monitor heart function to properly diagnose and treat various diseases and medical conditions. For example, a sensor placed within the chambers of the heart can be used to record variations in blood pressure based on physical changes to a mechanical element within the sensor. This information is then transferred through a wire from the sensor to an extracorporeal device that is capable of translating the data from the sensor into a measurable value that can be displayed. The drawback of this type of sensor is that there must be a wired connection between the sensor and the extracorporeal device, thus limiting Its use to acute settings.

Many types of wireless sensors have been proposed that would allow implantation of the device into the body. Then, through the appropriate coupling means, pressure reading can be made over longer periods of interest. The primary limitation to these type of sensors is that the fabrication methods used to manufacture them do not provide sufficient miniaturization to allow them to be introduced and implanted into the heart using nonsurgical, catheter based techniques while maintaining the ability to communicate wirelessly with external electronics.

An implantable sensor of this type must be assembled using the materials and fabrication methods that ensure appropriate biocompatibility and long term mechanical and electrical durability.

One method of manufacturing a sensor capable of measuring pressure is to use a capacitor that is assembled such that one of the capacitive plates will be displaced with respect to the other as a result of exposure to externally applied stress. This displacement will result in a change in the capacitance that is proportional to the applied stress. Various patents describe the fabrication and use of capacitor-based pressure sensors. The primary limitation of many of these inventions is that the techniques used to fabricate the sensors do not lend themselves to the miniaturization necessary for it to be configured as an implantable medical device while maintaining the capability of communicating wirelessly with external electronics.

The fabrication methodologies that have been developed in the field of Micro-Electro-Mechanical Systems ("MEMS"), however, do specifically provide the means for assembling miniaturized sensors capable of measuring a variety of properties including pressure. MEMS devices as described in prior patents traditionally use silicon as a substrate for construction of miniature electrical or mechanical structures.

A number of patents detail pressure sensors (some capacitive in nature, some manufactured using MEMS based fabrication methods) that are specifically designed for implantation into the human body. These sensors suffer from many of the limitations already mentioned, with the additional concerns that they require either the addition of a power source to operate the device or the need for a physical connection to a device capable of translating the sensor output into a meaningful display of a physiologic parameter.

To overcome the two problems of power and physical connection, the concept of a externally modulated LC circuit has been applied to development of implantable pressure sensors. Of a number of patents that describe a sensor design of this nature, U.S. Pat. No. 6,113,553 to Chubbuck is a representative example. The Chubbuck patent demonstrates how a combination of a pressure sensitive capacitor placed in series with an inductor coil provides the basis for a wireless, un-powered pressure sensor that is suitable for implantation into the human body. Construction of an LC circuit in which variations of resonant frequency correlate to changes in measured pressure and in which these variations can be detected remotely through the use of electromagnetic coupling are further described in U.S. Pat. Nos. 6,111,520 and 6,278,379, both to Allen et al., incorporated herein by reference.

The device described in the Chubbuck patent is large, thus requiring surgical implantation and thereby limiting its applicability to areas that are easily accessible to surgery (e.g., the skull).

Thus, the need exists for a miniature, biocompatible, wireless, un-powered, hermetic pressure sensor that can be delivered into the heart or the vasculature using a small diameter catheter.

Further, U.S. Pat. Nos. 6,111,520, 6,855,115 and U.S. Publication No. 2003/0136417, each of which is incorporated herein by reference, all describe wireless sensors that can be implanted within the body. These sensors can be used to monitor physical conditions within the heart or an abdominal aneurysm. An abdominal aortic aneurysm (AAA) is a dilatation and weakening of the abdominal aorta that can lead to aortic rupture and sudden death. In the case of a repaired abdominal aneurysm, a sensor can be used to monitor pressure within the aneurysm sac to determine whether the intervention is leaking. The standard treatment for AAAs employs the use of stent-grafts that are implanted via endovascular techniques. However, a significant problem that has emerged with these stent-grafts for AAAs is acute and late leaks of blood into the aneurysms sac. Currently, following stent-graft implantation, patients are subjected to periodic evaluation via abdominal CT (Computed Tomography) with IV contrast to identify the potential presence of stent-graft leaks. This is an expensive, risky procedure that lacks appropriate sensitivity to detect small leaks.

Typically, the sensors utilize an inductive-capacitive ("LC") resonant circuit with a variable capacitor. The capacitance of the circuit varies with the pressure of the environment in which the sensor is located and thus, the resonant frequency of the circuit varies as the pressure varies. Thus, the resonant frequency of the circuit can be used to calculate pressure.

Ideally, the resonant frequency is determined using a non-invasive procedure. Several examples of procedures for determining the resonant frequency of an implanted sensor are discussed in U.S. Pat. No. 6,111,520. Some of the procedures described in the patent require the transmission of a signal having multiple frequencies. A drawback of using a transmission signal having multiple frequencies is that the energy in the frequency bands outside the resonant frequency is wasted. This excess energy requires more power which results in an increase in cost, size, and thermal requirements, as well as an increase in electromagnetic interference with other signals. Thus, there is a need for an optimized method that is more energy efficient and requires less power.

There are unique requirements for communicating with an implanted sensor. For example, the system must operate in a low power environment and must be capable of handling a signal from the sensor with certain characteristics. For example, the signal from the sensor is relatively weak and must be detected quickly because the signal dissipates quickly. These requirements also impact the way that common problems are handled by the system. For example, the problems of switching transients and false locking need to be handled in a manner that accommodates the sensor signal characteristics. Thus, there is a need for a method for communicating with a wireless sensor that operates in a low power environment and that efficiently determines the resonant frequency of the sensor.

The resonant frequency of the sensor is a measured parameter that is correlated with the physical parameter of interest. To be clinically useful there must be means to ensure that variations in measurement environment do not affect the accuracy of the sensor. Thus, there is a need for a system and method for communicating with a wireless sensor that considers variations in the measurement environment.

SUMMARY

Stated generally, the present invention is directed toward a sensor and method for manufacturing a sensor to measure pressure within the heart or vasculature of a patient. The sensor comprises an upper wafer formed from a dielectric material, the upper wafer having one or more channels. The upper wafer includes a first capacitor plate and a second capacitor plate formed on a lower surface of the upper wafer. According to one embodiment the sensor further comprises an inductor formed from one or more windings of a conductive material, the inductor being contained within the one or more channels in the upper wafer in fixed relation to the first and second capacitor plates, the inductor comprising first and second inductor leads, the first lead being electrically coupled to the first capacitor plate and the second lead electrically coupled to the second capacitor plate. The apparatus further comprises a lower wafer formed from the dielectric material, the lower wafer being thinner than the upper wafer and a third capacitor plate formed on an inner surface of the lower wafer, the upper and lower wafers being fused together to form a monolithic housing such that the first and second capacitor plates are arranged in parallel, spaced-apart relation from the third capacitor plate, a portion of the lower wafer comprising a pressure sensitive deflective region underlying at least a portion of the third capacitor plate, whereby the deflective region deflects in response to changes in ambient pressure in the medium.

Generally the invention further comprises a method for manufacturing a sensor for measuring pressure within the heart or the vasculature of a patient by implanting a pressure sensor in such locations utilizing catheter-based endovascular or surgical techniques and using extracorporeal electronics to measure the pressure easily, safely, and accurately. Stated somewhat more specifically, according to a first aspect of manufacturing a sensor for in vivo applications, a recess is formed in a first wafer, and a capacitor plate is formed in the recess of the first wafer. A second capacitor plate is formed in a corresponding region of a second wafer. The two wafers are mutually imposed and affixed to one another such that the two capacitor plates are arranged in parallel, spaced-apart relation.

According to a second aspect of the invention, a method of manufacturing a sensor for in vivo applications comprises the step of providing three wafers of an electrically non-conductive material. First and second capacitor plates are formed on an upper surface of the first wafer. A third capacitor plate is formed on a lower surface of the second wafer. The first and second wafers are then mutually imposed such that the third capacitor plate is positioned in generally parallel, spaced-apart relation from the first and second capacitor plates. An inductor coil is positioned on top of an upper surface of the second wafer, and the leads of the inductor coil are electrically connected to the first and second capacitor plates. A cavity is formed in the third wafer sufficient to receive said inductor coil, and the third wafer is positioned on top of the second wafer with the inductor coil being received within the cavity of the third wafer. Finally, the second wafer is bonded to the first and third wafers.

According to still another aspect of the invention, a method of manufacturing a sensor for in vivo applications, comprises the steps of forming a bottom plate on a wafer of electrically insulating material, forming a sacrificial layer over the bottom plate, forming a top plate on top of the sacrificial layer, and removing the sacrificial layer to leave the bottom and top plates in spaced-apart relation.

In yet another aspect of the present invention, a method of manufacturing a sensor for in vivo applications includes the step of providing first and second wafers. A recess is formed in the first wafer, and a first plate is formed in the recess of the first wafer. A coil-receiving trench is formed in an upper surface of the second wafer, and second and third plates are formed on the upper surface of the second wafer within the perimeter of the coil-receiving trench. An inductor coil is positioned within the coil-receiving trench in the upper surface of the second wafer, and the leads of the inductor coil are electrically connected to the second and third plates on the upper surface of the second wafer. The first and second wafers are affixed to one another such that the first plate in the recess of the first wafer is in parallel, spaced apart relation to the second and third plates on the upper surface of the second wafer.

Thus it is an object of this invention to provide a method for manufacturing an implantable wireless sensor.

It is also an object of this invention to provide a method for manufacturing a wireless, passive micromechanical sensor that can be delivered endovascularly to a heart chamber or the vasculature.

It is a further object of this invention to provide a method for manufacturing an implantable, wireless, passive sensor that can be delivered endovascularly to a heart chamber or the vasculature to measure pressure and/or temperature.

Other objects, features, and advantages of the present invention will become apparent upon reading the following specification, when taken in conjunction with the drawings and the appended claims.

Further, a goal of aneurysm treatment is to depressurize the sac and to prevent rupture. Endoleaks, whether occurring intraoperatively or postoperatively, can allow the aneurysmal sac to remain pressurized and therefore, increase the chance of aneurysm rupture. The current imaging modalities angiography and CT scan are not always sensitive enough to detect endoleaks or stent graft failure. Intrasac pressure measurements provide a direct assessment of sac exclusion from circulation and may therefore offer intraoperative and post-operative surveillance advantages that indirect imaging studies do not.

In applications of embodiments herein, an AAA pressure sensor is placed into the aneurysm sac at the time of stent-graft insertion. The pressure readings are read out by the physician by holding an electronic instrument, which allows an immediate assessment of the success of the stent-graft at time of the procedure and outpatient follow-up visits, by reading the resonant frequency of the wireless sensor and correlating the frequency reading to pressure.

Embodiments herein meets the needs described above by providing a system and method for communicating with a wireless sensor to determine the resonant frequency of the sensor. The system energizes the sensor with a low duty cycle, gated burst of RF energy having a predetermined frequency or set of frequencies and a predetermined amplitude. The energizing signal is coupled to the sensor via a magnetic loop. The sensor may be an inductive-capacitive ("LC") resonant circuit with a variable capacitor that is implanted within the body and used to measure physical parameters, such as pressure or temperature. The energizing signal induces a current in the sensor which is maximized when the energizing frequency is the same as the resonant frequency of the sensor. The system receives the ring down response of the sensor via magnetic coupling and determines the resonant frequency of the sensor, which is used to calculate the measured physical parameter.

In one aspect, a pair of phase locked loops ("PLLs") is used to adjust the phase and the frequency of the energizing signal until its frequency locks to the resonant frequency of the sensor. In one embodiment, one PLL samples during the calibration cycle and the other PLL samples during the measurement cycle. These cycles alternate every 10 microseconds synchronized with the pulse repetition period. The calibration cycle adjusts the phase of the energizing signal to a fixed reference phase to compensate for system delay or varying environmental conditions. The environmental conditions that can affect the accuracy of the sensor reading include, but are not limited to, proximity of reflecting or magnetically absorbpative objects, variation of reflecting objects located within transmission distance, variation of temperature or humidity which can change parameters of internal components, and aging of internal components.

One of the PLLs is used to adjust the phase of the energizing signal and is referred to herein as the fast PLL. The other PLL is used to adjust the frequency of the energizing signal and is referred to herein as the slow PLL. During the time that the energizing signal is active, a portion of the signal enters the receiver and is referred to herein as a calibration signal. The calibration signal is processed and sampled to determine the phase difference between its phase and the phase of a local oscillator (referred to herein as the local oscillator 2). The cycle in which the calibration signal is sampled is referred to as the calibration cycle. The system adjusts the phase of the energizing signal to drive the phase difference to zero or another reference phase.

During the measurement cycle, the signal coupled from the sensor (referred to herein as the coupled signal or the sensor signal) is processed and sampled to determine the phase difference between the coupled signal and the energizing signal. The system then adjusts the frequency of the energizing signal to drive the phase difference to zero or other reference phase. Once the slow PLL is locked, the frequency of the energizing signal is deemed to match the resonant frequency of the sensor. The operation of the slow PLL is qualified based on signal strength so that the slow PLL does not lock unless the strength of the coupled signal meets a predetermined signal strength threshold.

The system also handles false locking and switching transients. A false lock occurs if the system locks on a frequency that does not correspond to the resonant frequency of the sensor. In one aspect of the invention, the system avoids false locks by examining how the phase difference signal goes to zero. If the slope of the phase difference signal relative to time meets a predetermined direction, e.g. positive, then the PLL is allowed to lock. However, if the slope of the phase difference signal relative to time does not meet the predetermined direction, e.g. it is negative, then the signal strength is suppressed to prevent a false lock.

Another aspect herein uses frequency dithering to avoid a false lock. A constant pulse repetition frequency can add spectral components to the sensor signal and cause a false lock. By randomly varying the pulse repetition frequency of the energizing signal, the sidebands move back and forth so that the average of the sidebands is reduced. Thus, the system locks on the center frequency rather than the sidebands.

In another aspect, phase dithering can be used to reduce switching transients. The phase of the energizing signal and a local oscillator (referred to herein as local oscillator 1) are randomly changed. Varying the phase of the energizing signal varies the phase of the coupled signal, but does not affect the phase of the transient signal. Thus, the average of the transient signal is reduced. Changing the resonant frequency of the coil as it is switched from energizing mode to coupling mode also reduces switching transients. The capacitors that are connected to the coil are switched between different modes to slightly change the resonant frequency in order to reduce switching transients.

These and other aspects, features and advantages may be more clearly understood and appreciated from a review of the following detailed description of the disclosed embodiments and by reference to the appended drawings and claims.

BRIEF DESCRIPTION OF THE DRAWINGS

FIG. 47 is a side cutaway view of a shaft of a delivery apparatus for implanting the sensor of FIG. 44.

FIG. 48 is a side view of a tether wire of a delivery apparatus for implanting the sensor of FIG. 44.

FIG. 49 is a side view of a core wire of a delivery apparatus for implanting the sensor of FIG. 44.

FIG. 50 is a side view of a guidewire of a delivery apparatus for implanting the sensor of FIG. 44.

FIG. 51 is a side cutaway view of a delivery apparatus comprising the components of FIGS. 47-50 with the sensor of FIG. 44 mounted thereto.

FIG. 53A is a graph illustrating an exemplary energizing signal in accordance with an embodiment of the invention.

FIGS. 53B, 53C and 53D are graphs illustrating exemplary coupled signals in accordance with an embodiment of the invention.

DETAILED DESCRIPTION

Figure 1:
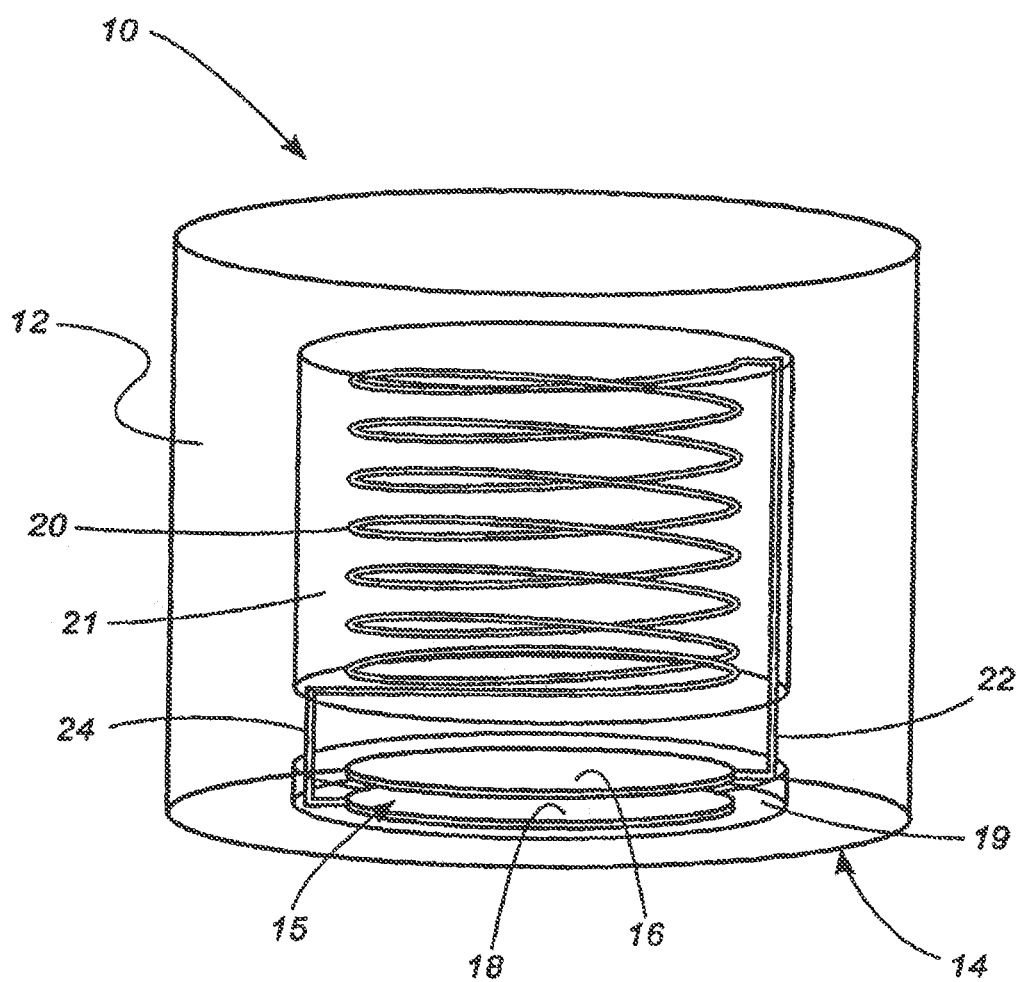
FIG. 1 is a perspective view of a first embodiment of an implantable wireless sensor according to the present invention, with the sensor body shown as transparent to reveal interior detail.

Referring now to the drawings, in which like numerals indicate like elements throughout the several views, FIG. 1 illustrates a sensor 10 for the measurement of physical parameters. The sensor can be fabricated using micromachining techniques and is small, accurate, precise, durable, robust, biocompatible, and insensitive to changes in body chemistry, or biology. Additionally, the sensor can incorporate radiopaque features to enable fluoroscopic visualization during placement within the body. Furthermore, this sensor is encased in a hermetic, unitary package of electrically insulating material where the package is thinned in one region so as to deform under a physiologically relevant range of pressure. The LC circuit contained in the packaging is configured so that one electrode of the capacitor is formed on the thinned region. This sensor does not require the use of external connections to relay pressure information externally and does not need an internal power supply to perform its function. The pressure sensor of the current invention can be attached to the end of a catheter to be introduced into a human body and delivered to an organ or vessel using catheter-based endovascular techniques.

Referring to FIG. 1, the sensor 10 includes a body 12. The body 12 is formed from electrically insulating materials, preferably biocompatible ceramics. In a preferred embodiment, the body is comprised of fused silica. The sensor 10 comprises a deflectable region 14 at the lower end of the body 12. The body 12 further comprises a lower chamber 19 and an upper chamber 21.

An LC resonator is hermetically housed within the body 12 and comprises a capacitor 16 and an inductor 20. As used herein, the term "hermetic" will be understood to mean "completely sealed, especially against the escape or entry of air and bodily fluids." The capacitor 15 is located within the lower cylindrical chamber 19 and comprises at least two plates 16, 18 disposed in parallel, spaced apart relation. The inductor 20 comprises a coil disposed within the upper chamber 21 and which is in conductive electrical contact with the capacitor 15.

The lower capacitor plate 18 is positioned on the inner surface of the deflectable region 14 of the sensor body 12. The upper capacitor plate 16 is positioned on a fixed region of the sensor body 12. A change in ambient pressure at the deflectable region 14 of the sensor 10 causes the deflectable region 14 to bend, thereby displacing the lower plate 16 with respect to the upper plate 18 and changing the capacitance of the LC circuit. Because the change in capacitance of the LC circuit changes its resonant frequency, the resonant frequency of the sensor 10 is pressure-dependent.

Beyond what has been presented in U.S. Pat. Nos. 6,111,520 and 6,278,379, covering the fundamental operating principle of the wireless pressure sensor, additional means to further sensor miniaturization is required in order to achieve an acceptable size for implantation into the heart or the vasculature. The sensor outer dimensions are constrained by the lumen size of the delivery catheter that is used to introduce the sensor. Catheter inner diameters typically range from 1-5 mm. Also, the size and shape of the sensor should minimally interfere with mechanical or hemodynamic function of the heart or vessel where it is located.

Within these physical size constraints, one of the most significant challenges is achieving adequate coupling to the sensor inductor coil from the external readout device at the necessary distance from the outside of the body to the implant site. One method for achieving enhanced coupling is to add magnetic material to the inductor. However, this approach is not feasible in a sensor intended for in vivo use, as the magnetic material would be adverse to magnetic resonance imaging, for example. For a limited coil cross-sectional area, an increased coupling coefficient is also achievable by using a three-dimensional inductor coil configuration, as opposed to two-dimensional designs. For these reasons, a three-dimensional helical inductor coil configuration 20 is the preferred embodiment for the sensor design.

The disclosed sensor features a completely passive inductive-capacitive (LC) resonant circuit with a pressure varying capacitor. Because the sensor is fabricated using completely passive electrical components and has no active circuitry, it does not require on-board power sources such as batteries, nor does it require leads to connect to external circuitry or power sources. These features create a sensor which is self-contained within the packaging material and lacks physical interconnections traversing the hermetic packaging, such interconnects frequently being cited for failure of hermeticity. Furthermore, other sensing capabilities, such as temperature sensing, can be added using the same manufacturing techniques. For example, temperature sensing capability can be accomplished by the addition of a resistor with known temperature characteristics to the basic LC circuit.

The capacitor in the pressure sensor of the disclosed invention consists of at least two conductive elements separated by a gap. If a force is exerted on the sensor, a portion of the sensor deflects, changing the relative position between the at least two conductive elements. This movement will have the effect of reducing the gap between the conductive elements, which will consequently change the capacitance of the LC circuit. An LC circuit is a closed loop system whose resonance is proportional to the inverse square root of the product of the inductor and capacitor. Thus, changes in pressure alter the capacitance and, ultimately, cause a shift in the resonant frequency of the sensor. The pressure of the environment external to the sensor is then determined by referencing the value obtained for the resonant frequency to a previously generated curve relating resonant frequency to pressure.

Because of the presence of the inductor, it is possible to couple to the sensor electromagnetically and to induce a current in the LC circuit via a magnetic loop. This characteristic allows for wireless exchange of electromagnetic energy with the sensor and the ability to operate it without the need for an on-board energy source such as a battery. Thus it is possible to determine the pressure surrounding the sensor by a simple, non-invasive procedure by remotely interrogating the sensor, recording the resonant frequency, and converting this value to a pressure measurement.

One method of sensor interrogation is explained in U.S. patent application Ser. No. 11/105,294, incorporated herein by reference. According to this invention, the interrogating system energizes the sensor with a low duty cycle, gated burst of RF energy having a predetermined frequency or set of frequencies and a predetermined amplitude. The energizing signal is coupled to the sensor via a magnetic loop. The energizing signal induces a current in the sensor that is maximized when the frequency of the energizing signal is substantially the same as the resonant frequency of the sensor. The system receives the ring down response of the sensor via magnetic coupling and determines the resonant frequency of the sensor, which is then used to determine the measured physical parameter. The resonant frequency of the sensor is determined by adjusting the frequency of the energizing signal until the phase of the ring down signal and the phase of a reference signal are equal or at a constant offset. In this manner, the energizing signal frequency is locked to the sensors resonant frequency and the resonant frequency of the sensor is known. The pressure of the localized environment can then be ascertained.

Q factor (Q) is the ratio of energy stored versus energy dissipated. The reason Q is important is that the ring down rate of the sensor is directly related to the Q. If the Q is too small, the ring down rate occurs over a substantially shorter time interval. This necessitates faster sampling intervals, making sensor detection more difficult. Also, as the Q of the sensor increases, so does the amount of energy returned to external electronics. Thus, it is important to design sensors with values of Q sufficiently high enough to avoid unnecessary increases in complexity in communicating with the sensor via external electronics.

The Q of the sensor is dependent on multiple factors such as the shape, size, diameter, number of turns, spacing between the turns and cross-sectional area of the inductor component. In addition Q will be affected by the materials used to construct the sensors. Specifically, materials with low loss tangents will provide a sensor with higher Q factors.

The body of the implantable sensor of the disclosed embodiment of the present invention is preferably constructed of ceramics such as, but not limited to, fused silica, quartz, pyrex and sintered zirconia, that provide the required biocompatibility, hermeticity and processing capabilities. These materials are considered dielectrics, that is, they are poor conductors of electricity but are efficient supporters of electrostatic or electroquasistatic fields. An important property of dielectric materials is their ability to support such fields while dissipating minimal energy. The lower the dielectric loss, the lower the proportion of energy lost, and the more effective the dielectric material is in maintaining high Q.

With regard to operation within the human body, there is a second important issue related to Q, namely that blood and body fluids are conductive mediums and are thus particularly lossy. As a consequence, when a sensor is immersed in a conductive fluid, energy from the sensor will dissipate, substantially lowering the Q and reducing the sensor-to-electronics distance. It has been found that such loss can be minimized by further separation of the sensor from the conductive liquid. This can be accomplished, for example, by coating the sensor in a suitable low-loss-tangent dielectric material. The potential coating material must also meet stringent biocompatibility requirements and be sufficiently compliant to allow transmission of fluid pressure to the pressure-sensitive deflective region. One preferred material for this application is silicone rubber. It should be appreciated that use of a coating is an optional feature and is not required to practice the invention per se but such coatings will preserve the Q of the sensor which can prove advantageous depending on the intracorporeal location of the sensor.

There are various manufacturing techniques that can be employed to realize sensors according to the current invention. Capacitors and inductors made by a variety of methods can be manufactured separately, joined through interconnect methods and encapsulated in hermetic packaging. In one embodiment, the pressure sensitive capacitor 15 and the three-dimensional inductor coil 20 are formed separately and joined together to form the LC circuit. In another embodiment, the capacitor and inductor coil can be manufactured integral with one another. Additionally, there are several methods to create these discrete elements and to join each discrete element to create the final sensor. The following examples are provided to illustrate important design considerations and alternative methods for creating these discrete sensor elements but should not be construed as limiting the invention in any way.

Figure 12:
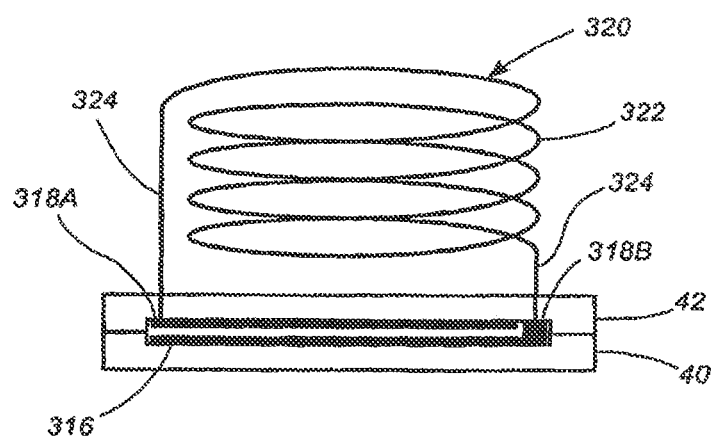
FIG. 12 is a schematic view of still another embodiment of an implantable, wireless pressure sensor.

Referring to FIG. 12, the inductor coil 320 is comprised of the inductor coil body 322 and the coli leads 324. Numerous parameters of the inductor coil can be varied to optimize the balance of size and electrical properties of the circuit, including the materials, coil diameter, wire gage, insulation thickness, number of coil windings, and cross-sectional area of the coil body. The material comprising the coil must be highly conductive and also biocompatible. Suitable materials include, but are not limited to, gold, copper, and alloys thereof.

It is preferable in the practice of the disclosed invention to minimize or eliminate changes in resonant frequency of sensors of the invention due to factors other than capacitance in order to reliably correlate the shift in resonant frequency with a change in distance between the capacitor plates. Thus, it is important that the inductor coil 320 in sensors of the current invention maintain a high degree of mechanical stability as a change in coil position relative to the capacitor or a change in coil configuration will cause the resonant frequency of the device to change. There are many ways to immobilize the inductor coil 320 of the present invention. If the wire used to construct the coil is sufficiently strong, the coil can be self-supporting, also known as an "air core" configuration. A solenoid coil is another suitable configuration. If the wire is not sufficiently strong to maintain its intended configuration during assembly and in use, the coil can be formed around a central bobbin comprised of a suitable material. Such bobbins can be configured to be mechanically fixed to any surface or combination of surfaces defining the coil receiving trench via a press fit. Alternatively, the coil can be wound on a thermoplastic bobbin where the thermoplastic material can be subjected to sufficient heat to cause flow to encapsulate and/or adhere to the surface of the coil receiving trench.

Alternatively, a thermosetting or thermoplastic polymer with good high temperature characteristics, low loss tangent, and, optionally, low dielectric constant material can be used to support the coil. The polymer should also be highly inert, have excellent aging resistance and exhibit substantially no moisture absorbance or outgassing. With the use of a thermosetting material, the polymer is applied to the coil in liquid form and allowed to cure or otherwise harden. Thermoplastic materials can be preformed and inserted between the coil and at least one coil receiving trench wall and subsequently heated to achieve sufficient flow to encapsulate and/or adhere to the coil and at least one coil receiving trench wall.

Polyimide, fluorinated polymers, glass frit, ceramic paste and liquid crystal polymer are examples of suitable materials for immobilizing the inductor coil 320 due to their thermal, electrical, and mechanical properties. However, manufacturing processes achieving substantially similar results that involve lower processing temperatures would make other material choices desirable, such choices being obvious to one skilled in the art.

The wire from which the coil is formed can be solid wire, bundled wire or cable, or individually insulated stranded wire.

The wire gage, coil diameter, cross-sectional area of the coil body, and number of windings all influence the value of inductance and the detection range of the circuit. As any of these properties increase, so do the size and the inductance of the coil, as well as the sensor-to-electronics distance. To specify an inductor coil for use in the sensor, size considerations must be balanced with those of inductance and Q.

A small scale three-dimensional inductor coil can be formed in a variety of ways. It can be created conventionally. One such method is machine coil winding of small diameter insulated magnet wire, as shown in FIG. 1.

Figure 13:
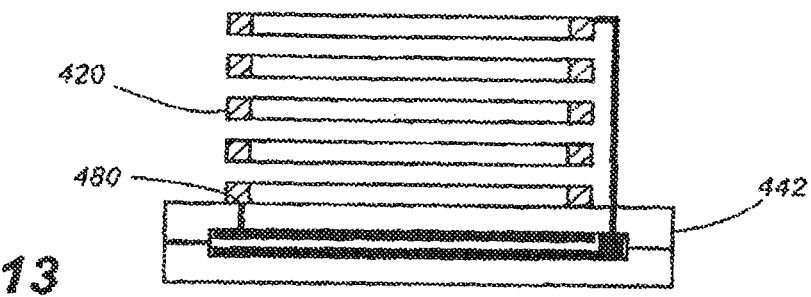
FIG. 13 is a schematic view of a further embodiment of an implantable, wireless pressure sensor in which a three-dimensional inductor coil is built onto the top of through connection terminals on the backside of a capacitor plate substrate.

In another embodiment, shown in FIG. 13, a three-dimensional inductor coil 420 is built onto the top of one of the through connections terminals 480 on the backside of the capacitor plate substrate 442, using integrated circuit processing techniques and a multitude of layers. This coil 420 can be defined and supported by photo-definable dielectric material such as photo-definable polyimide. In the disclosed embodiment, the coil is free standing in air, supported by same-material mechanical elements that are strategically positioned to minimize the effect of the supporting mechanical elements on the electrical function of the coil.

Figure 14:
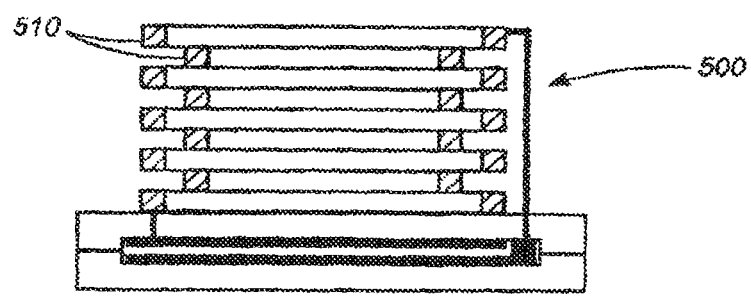
FIG. 14 is a schematic view of another embodiment of a wireless pressure sensor in which each subsequent layer is alternately spaced slightly smaller or larger in diameter than the previous winding.

In this approach it is desirable to minimize the number of design layers to improve batch process yield and to reduce processing time. In a conventional configuration, such as that shown in FIG. 13, a spacing layer is required between each winding, making the number of layers required equal to two times the number of windings. In one version 500 of the three-dimensional coil design, an example of which is shown in FIG. 14, each subsequent coil 510 is alternately spaced slightly smaller or larger in diameter than the previous winding. This configuration creates a small separation between adjacent coils 510 in the x-y plane, eliminating the need for an extra vertical spacing layer in between windings. This configuration results in a number of coil windings equal to the number of layers, which is more practical for manufacturing using a MEMS approach.

Figure 15:
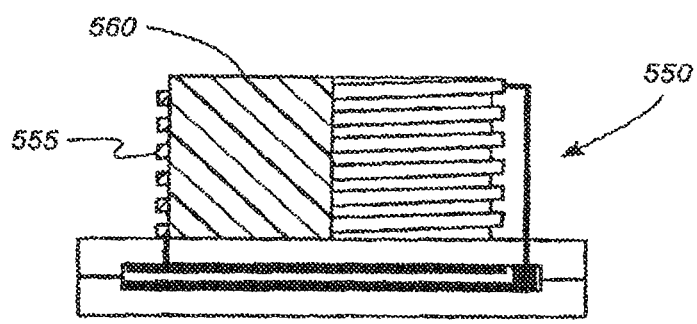
FIG. 15 is a schematic view of a further embodiment of an implantable, wireless pressure sensor in which a three-dimensional inductor coil is built onto the surface of a cylinder.

In yet another embodiment 550, shown in FIG. 15, a three-dimensional inductor coil 555 is built onto the surface of a cylinder 560 of an appropriate material such as, but not limited to fused silica. A conductive layer is first applied to the surface of the cylinder 560. Then a mold is formed onto the surface so that parts of the underlying conductive surface are exposed and some are covered. A metal may then be formed onto the exposed areas by electroplating, sputtering or vapor deposition. The exposed area forms a helical trench that extends along the surface of the cylinder, thus realizing an inductor coil.

Figure 2:
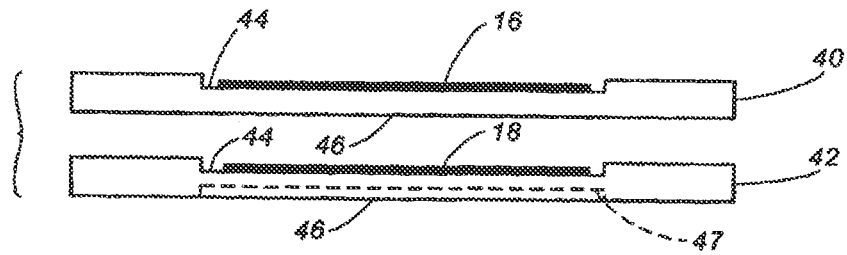
FIG. 2 is a schematic view of two pressure sensitive capacitor plates being formed in recessed trenches on two substrate wafers.

Referring now to FIG. 2, the pressure sensitive capacitor plates 16, 18 are formed on two separate substrate wafers 40, 42 in recessed trenches 44. At least one of the wafers 40 has a substrate thickness in the region 46 of the capacitive plate 16 such that sufficient pate deflection occurs due to external pressure change, resulting in a sufficient change in resonant frequency per unit pressure (mm Hg) once the LC circuit has been created. If necessary, the thickness of the wafer 40 in the region 46 can be reduced by suitable chemical or mechanical means, as indicated by the dashed line 47, to provide the desired range of deflection.

Figure 3:
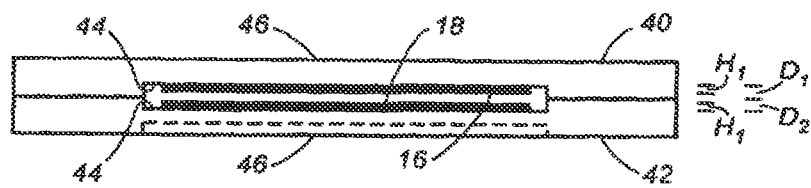
FIG. 3 is a schematic view showing the wafers of FIG. 2 imposed in face-to-face relation.

As shown in FIG. 3, the wafers 40, 42 are bonded together such that the capacitive plates are 16, 18 parallel and separated by a gap on the order of 0.1-10 microns, preferably 0.1-2 microns.

The performances of the sensor, especially the propensity of its capacitance and, in turn, its resonant frequency to change as a response to an environmental pressure change, are closely related to few fundamental geometrical considerations. Widening or elongating the deflective region will augment its mechanical flexibility, and, in turn, the pressure sensitivity of the sensor. Decreasing the thickness of the deflective area will result in similar improvements. However, thinner deflective region can become too fragile or otherwise more sensitive to systemic response from the host-organism other than changes in mean and pulsatile blood pressure (ex: hyperplasia, tissue overgrowth, etc.). Reducing the gap, while maintaining adequate deflective region thickness, offers a complementary alternative to insufficiently low sensitivity. As the initial value of the gap is shrinking, the motion of the deflective region relative to the initial gap becomes proportionally more important. This results in a greater change in capacitance for a given stimulus, therefore enhancing the pressure sensitivity. While relevant sensitivity can be achieved with initial air-gap ranging from 0.1 to 10 micrometers, initial air-gaps ranging from a 0.1 to 2 micrometers are preferable.

To ensure adequate pressure range, the value of the maximum deflection under maximum load (indexed, for example, on physiologically relevant maximum pulsatile blood pressure values, at relevant location in the host-organism) ought to be, in theory, inferior or equal to the value of the initial gap. In practice, limiting the maximum deflection under maximum bad to represent only a fraction of the initial gap (ex: 0.6 micrometer for a 1 micrometer initial gap) will ease the fabrication constraints and result in a more robust and versatile sensor.

One suitable method for creating the pressure sensitive capacitor is by electroplating the individual plates 16, 18 in the recessed trenches 44 on a substrate wafer 40, 42 to a given height H1, H2 that is less than or equal to the depth D1, D2 of the respective trench 44. When the wafers are bonded together the capacitive plates are generally separated by the difference between the sum of the trench depths and the sum of the plate heights, (D1+D2)−(H1+H2). An inherent variation in the height of the plates and the required range of deflection for the full operating pressure range are parameters, which determine the initial separation distance (a.k.a. the gap).

Figure 4:
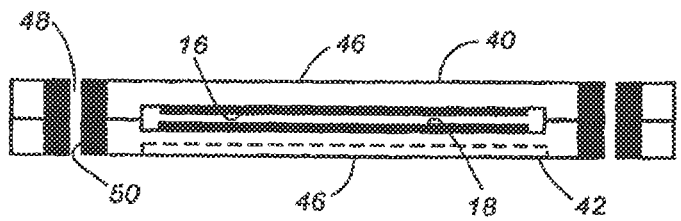
FIG. 4 is a schematic view showing the imposed wafers of FIG. 3 being laser-cut around their peripheries.

FIG. 4 illustrates the assembled wafers and capacitor plates laser-cut around their peripheries 48, reducing the capacitor to its final size and hermetically fusing the two wafers together at 50. A $CO_2$ laser can be used at a peak wavelength of about 10 microns if the substrate is fused silica. Power must be sufficiently large to cut and fuse the wafers together, while at the same time being sufficiently small that the internal components of the sensor are not damaged by excessive heat.

In an alternate method, the wafers are pre-bonded using glass frit to produce a hermetic seal around the cavities. In this method, the laser cut only releases the sensors from the wafer, and does not provide the primary means of creating the hermetic seal. Other suitable methods of hermetically sealing the wafers include, but are not limited to, adhesives, gold compression bonding, direct laser bonding, and anodic bonding.

Figure 5:
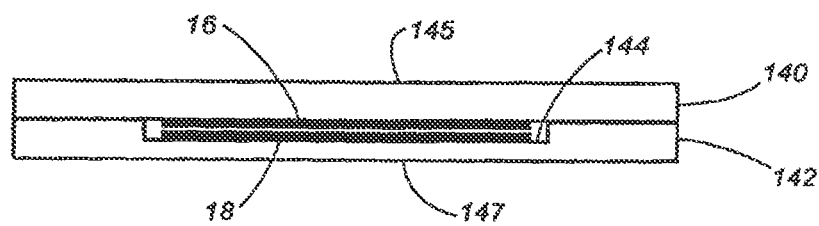
FIG. 5 is a schematic view of an alternate embodiment of two imposed wafers in which only one of the wafers has a recessed trench.

In an alternate embodiment illustrated in FIG. 5, one plate 18 is formed on a substrate wafer 142 having a trench 144 with a depth greater that of the trench 44 in the substrate wafer 40. The other plate 16 is formed on the inner surface of a wafer 140 without a trench. When imposed in face-to-face relation, the plate 16 is received into the lower end of the trench 144 with the plates 16, 18 disposed in parallel, spaced-apart relation.

Figure 6:
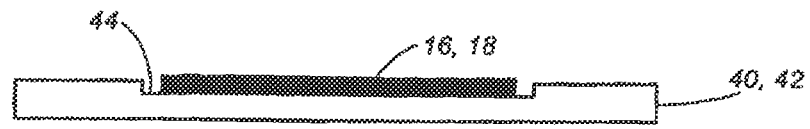
FIG. 6 is a schematic view illustrating a first step in a process for manufacturing wafers with capacitor plates formed thereon.
Figure 9:
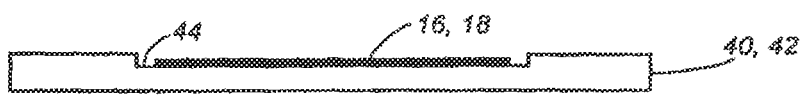
FIG. 9 is a schematic view illustrating a fourth step in a process for manufacturing wafers with capacitor plates formed thereon.

To achieve smaller gap separation distances on the order of 0.1-2 microns, revised processing methods are employed to bring additional control to the variation in height across the conductive plates 16, 18. One method is as follows: the conductive plate 16, 18 is built to a target height that slightly exceeds the depth of the recess trench 44, as shown in FIG. 6. In the disclosed embodiment the plates are formed by electroplating. Preferred materials for the plates are copper, gold, and alloys thereof. After building the plates, each conductive plate 16, 18 is polished using chemical/mechanical polishing (CMP) to planarize and reduce the height of the plate until it is less than the depth of the trench by the desired amount, as shown in FIG. 9.

Figure 7:
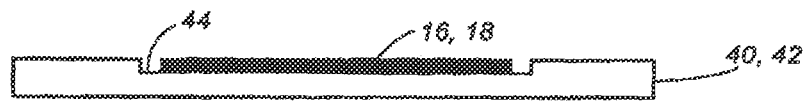
FIG. 7 is a schematic view illustrating a second step in a process for manufacturing wafers with capacitor plates formed thereon.
Figure 8:
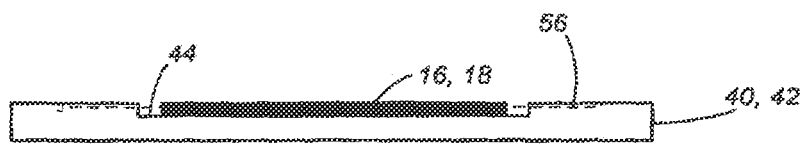
FIG. 8 is schematic view illustrating a third step in a process or manufacturing wafers with capacitor plates formed thereon.

Another method also begins with the plates 16, 18 formed to a height that slightly exceeds the depth of the trenches 44, as shown in FIG. 6. The metal capacitor plates 16, 18 are mechanically polished to planarize the metal surface down to the surface of the substrate 40, 42, as shown in FIG. 7. Following this step, the metal plates are chemically etched by a selective etchant to the height indicated by the dashed line 56 in FIG. 8 to achieve the desired difference in height between the height of the plate 16, 18 and the depth of the trench 44, as shown in FIG. 9.

Still another method for forming the plates is physical vapor deposition (PVD), also known as thin film deposition, in conjunction with photolithography. PVD is used to deposit a uniform layer of metal, sub-micrometer to tens of micrometers thick, on a wafer. Subsequently a layer of photoresist is deposited, a mask is used to pattern the photoresist, and a selective etching technique is utilized to etch away the extra metal and to define the desired pattern. Other methods of defining the metal pattern can be utilized, such as, shadow masking, a method well known in the art.

Figure 10:
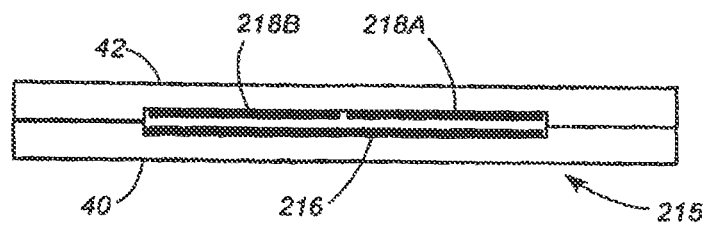
FIG. 10 shows another embodiment in which two capacitor plates are formed on one wafer.
Figure 11:
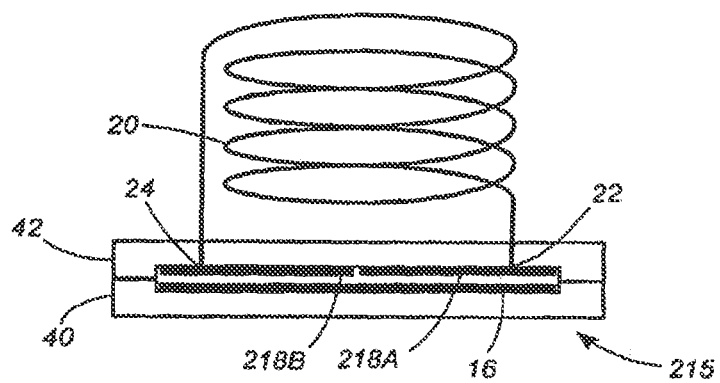
FIG. 11 Illustrates the embodiment of FIG. 10 showing the two capacitor plates on the single wafer connected to opposite ends of a helical inductor coil.

In one approach, shown in FIGS. 10 and 11, a pressure sensitive capacitor 215 can be formed by separating the bottom conductive pad into two separate regions 218A, 2186 that capacitively couple to one another via a common third conductive region 216 on the pressure sensitive deflective region. The inductor coil 20 is then electrically connected as shown in Ha 11, one lead 22 of the coil 20 to the first region 218A, and the other lead 24 of the coil 20 to the second region 2186.

When the split-plate design is employed for one side of the capacitor, as shown in FIG. 11, the spat plates 218A, 218B are preferably located on the fixed side of the capacitor (i.e., opposite the pressure-sensitive side), because the electrical/mechanical interconnects made to the spot plates in order to complete the LC circuit are less prone to mechanical failure when the surface to which they are mechanically attached does not deflect or move repetitively.

In yet another embodiment, shown in FIG. 12, the plate on the top wafer 42 is separated by a dielectric into two conductive regions 318A, 318B, with one region 318B substantially larger than the other 318A. After bonding together of the two wafers 40, 42, the smaller conductive region 318A is electrically connected to the outer edge of the pressure sensitive plate 316, spanning the air gap with a laser weld that is performed through the substrate material. The laser wavelength is selected so that it is passes through the substrate material with minimal energy absorption, but heats the conductive plate sufficiently to produce the weld connection between the top and bottom plates 316, 318A.

It will be appreciated that sensors embodied by the current invention can have capacitive and inductive elements maintained in separate hermetic cavities or that these elements may be contained in a single hermetic cavity.

Figure 22:
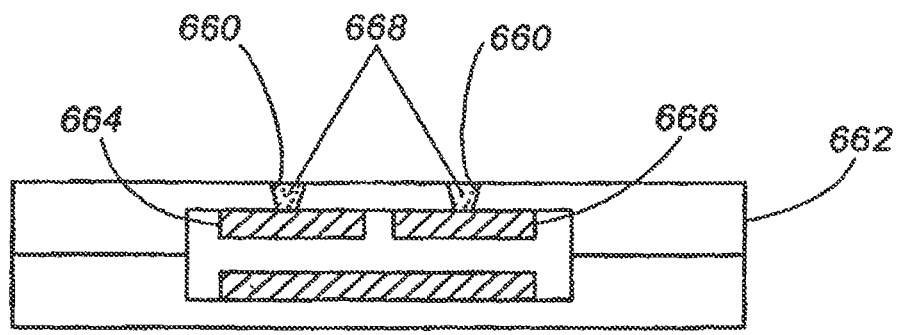
FIG. 22 shows a first arrangement for electrically and mechanically interconnecting a capacitor plate to an inductor coil.

In one embodiment, the pressure sensitive capacitor 15 needs to be connected to the three-dimensional inductor coil 20 while maintaining a hermetic seal around the internal cavity that defines the separation gap between the capacitive plates 16, 18. This can be achieved by using a variety of through-wafer interconnection methods, familiar to those skilled in the art. Referring to FIG. 22, through holes or vias 660 are formed in an upper wafer 662 to provide mechanical and electrical access to a pair of upper capacitor plates 664, 666. The wafer through-holes can be formed before or after plate formation using some combination of the following techniques: laser drilling, chemical (wet) etching, conventional or ultrasonic machining, or dry etching. As shown in FIG. 22, the vies 660 can optionally be filled with gold, copper, or other suitable conductive material to form through-wafer interconnects 668 in conductive communication with the capacitor plates 664, 666. The through-wafer interconnects 668 thus form a hermetic seal. Leads from an inductor coil (not shown) are attached to the through-wafer interconnects 668 to place the leads m conductive communication with the capacitor plates 664, 666.

Figure 23:
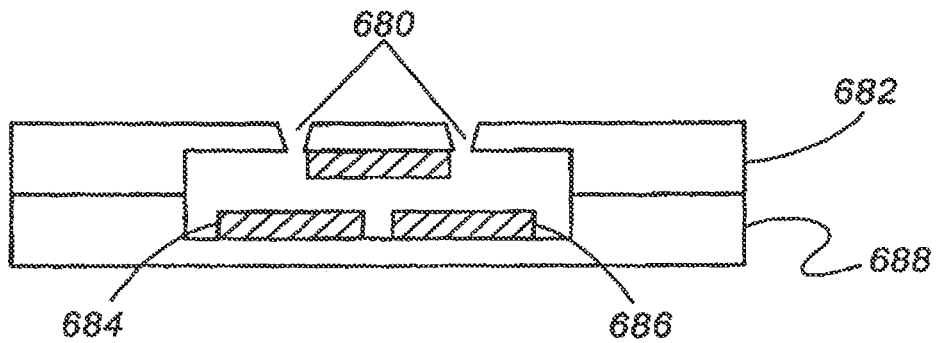
FIG. 23 shows a second arrangement for electrically and mechanically interconnecting a capacitor plate to an inductor coil.

Referring to FIG. 23, through holes or vies 680 are formed In an upper wafer 682 to provide mechanical and electrical access to a pair of lower capacitor plates 684, 686. Electrical connections to the lower capacitor plates 684, 686 will be accomplished through leads of the inductor coil (not shown) or through wires or other suitable conductive means.

Thermosonic or ultrasonic bonding can be used to connect the inductor coil to either an electrode of a capacitor or a through-wafer interconnect. Thermosonic and ultrasonic bonding are types of wire bonding used for metal wires including, but not limited to, gold wires. Typical temperatures required for thermosonic bonding are between 125-220.degree. C., and bonding occurs when a combination of static and ultrasonic mechanical and thermal energy is delivered to the metallic coil wire to be bonded to a metal surface. Ultrasonic bonding is performed just as thermosonic bonding but without the use of heat. Useful materials for the metallized bond sites and coil comprise gold, copper and aluminum and alloys thereof. Bonds can be formed between certain dissimilar metals as well as between all like metals, and such combinations are widely known in the art.

If the metal or metal alloy used for the coil has a dielectric (e.g., polymer) coating, the coating must be removed prior to bonding. The coating can be removed to expose the metal at the adhesion point so that bonding can occur by either mechanical or chemical means. Alternatively, the parameters (e.g. time, heat, pressure) of the thermosonic bonding process can be altered and the geometry of the bonding tool modified so that reliable mechanical and electrical interconnects are created. Such modifications cause the coating material to be pushed aside, exposing the metal at the bonding site and extruding the wire slightly. This latter technique provides certain advantages because it reduces the number of manufacturing steps.

An alternate method of conductively connecting the coil to the capacitive plates is the solder bump. Solder is applied to the metal-metal interface of the coil and electrode or interconnect to form a mechanical and electrical connection. This method can be used for capacitor plate or through-wafer interconnections. Lead-free solder should be used for biocompatibility. Connection can also be achieved through IC processing techniques, which allow for plates and coils to be formed in electrical contact with one another. Finally laser welds, as previously discussed, can be used to achieve electrical/mechanical interconnects.

Figure 16:
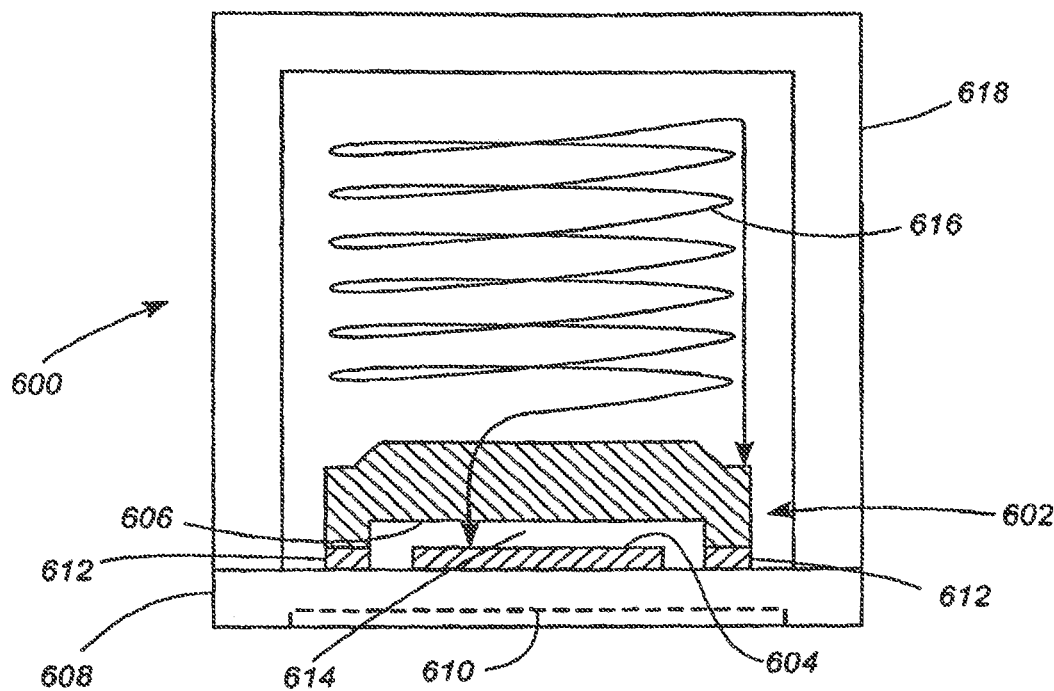
FIG. 16 is a schematic view of another embodiment of a wireless pressure sensor in which the pressure sensitive capacitor and three-dimensional inductor coil are formed together on one wafer.

FIG. 16 illustrates a surface micromachined, capacitor coupled sensor 600. The capacitor structure 602 comprises at least two plates 604, 606, at least one 604 of which is built directly atop a first wafer 608. This plate 604 will be referred to as the bottom plate. The region of the wafer 608 where the bottom plate 604 is built will be referred to as the deflective region 610. If necessary, the thickness of the wafer 608 in the region of the deflective region 610 can be reduced in thickness to enhance its deformability.

The other plate 606 is suspended above the bottom plate 604. The top plate 606 is mechanically anchored to the deflective region by pillar-like supporting elements 612 located at the periphery of the bottom plate 604. Bottom and top plates 604, 606 are electrically insulated and physically separated from one another by an air gap 614. The top electrode 606 mechanical design, material and dimensions are carefully chosen so that the suspended part of the electrode does not structurally deform under its own weight or creep over time.

A coil 616 of relevant geometry and inductance value is built or assembled using, as an example, any of the methods described herein. Its terminals are electrically and mechanically connected to either one of the opposite plates 604, 606 of the capacitor 602. A capsule 618 or other form of hermetic surrounding is used to encapsulate both the coil 616 and capacitor 602.

To achieve the desired pair of fixed and suspended plates 604, 606, the fabrication process of the disclosed embodiment employs a technique known in the art as "sacrificial layer." A sacrificial layer is a structural layer that remains buried throughout the fabrication process under various layers of material until it can be removed, releasing the structures and layers built on top of the sacrificial layer. Once removed, a void remains in place of the sacrificial layer. This void forms the air gap that separates top from bottom plate(s).

A sacrificial layer must abide by at least two rules: (1) it must remain unaffected (no cracking, peeling, wrinkling, etc.) during the entire fabrication process until it is removed, and (2) selective and efficient removal techniques must exist to remove it without adverse consequences to any remaining structures.

Figure 17:
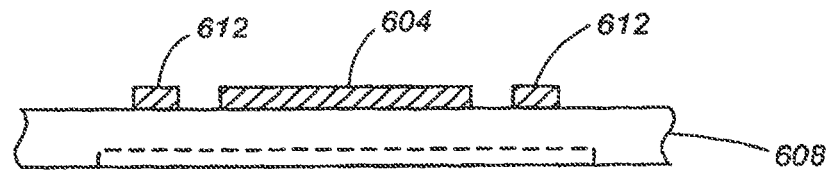
FIG. 17 is a schematic view showing a first step in the manufacturing process of the wireless pressure sensor of FIG. 16.

Referring now to FIG. 17, the fabrication of the capacitor 602 starts with the creation of the bottom plate 604 on the wafer 808, using physical vapor deposition and photolithography. The backside of the wafer 608 is optionally thinned to enhance compliance in the deflective region 610 of the wafer at the location of the bottom plate 604 so as to facilitate deflection when a force or a pressure is applied.

The anchoring sites 612 are defined at the periphery of the bottom plate 604. Anchoring sites 612 are small enough to represent only a fraction of the footprint of either bottom or top plate 604, 606. However, they are big enough to insure reliable mechanical anchoring for the top plate 606.

Figure 18:
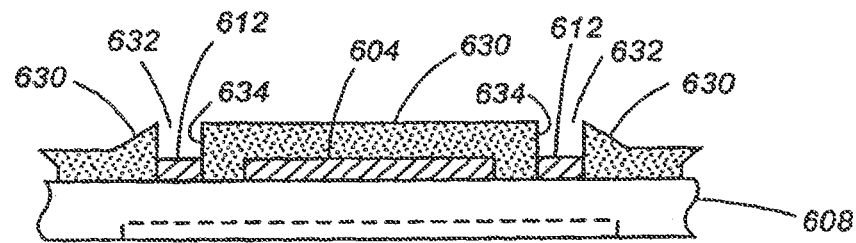
FIG. 18 is a schematic view showing a second step in the manufacturing process of the wireless pressure sensor of FIG. 16.

Referring now to FIG. 18, a layer 630 of material with desirable physical and chemical traits is deposited onto the wafer 608 over the bottom plate 604 and the anchoring sites 612 to serve as a sacrificial layer. The sacrificial material is, but is not limited to, a thin film of photo-definable polymer (the first polymer layer). The thickness of the polymer is tuned by altering the conditions during deposition. Film thicknesses ranging from fractions of micrometers to tens of micrometers are achieved routinely. To ensure that the layer 630 of photo-definable polymer remains unaffected (no cracking, peeling, wrinkling, etc.) during the entire fabrication process until it is removed, proper curing and cross-linking precautionary steps must be taken.

With further reference to FIG. 18, using photolithography, windows 632 are opened in the first polymer layer 630. The window geometry and in-plane location corresponds to those of the anchoring sites 612. Because the photo-definable polymer has a non-null thickness, each opening (a.k.a. window) in the first polymer layer is surrounded by sidewalls 634 which height corresponds to the thickness of the first polymer layer.

Figure 19:
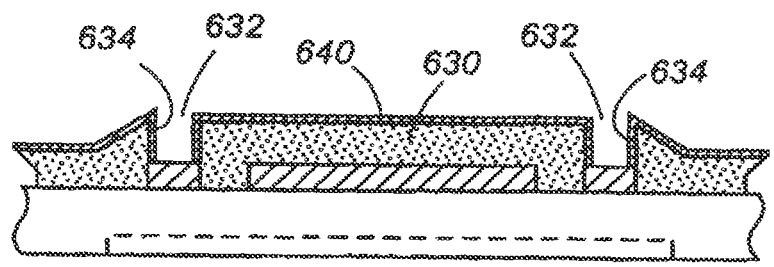
FIG. 19 is a schematic view showing a third step in the in a manufacturing process of the wireless pressure sensor of FIG. 16.

A thin film metallic layer 640 is then deposited on top of the sacrificial layer 630, as depicted in FIG. 19. This layer comprises a seed layer, as it will provide a site upon which electroplated metals can grow later on. The method of deposition should insure that the metallic film 640 evenly coats the upper surface of the sacrificial layer 630 (the first polymer layer) as well as the sidewall 634 and the bottom areas of the windows 632 previously defined in the sacrificial layer.

Figure 20:
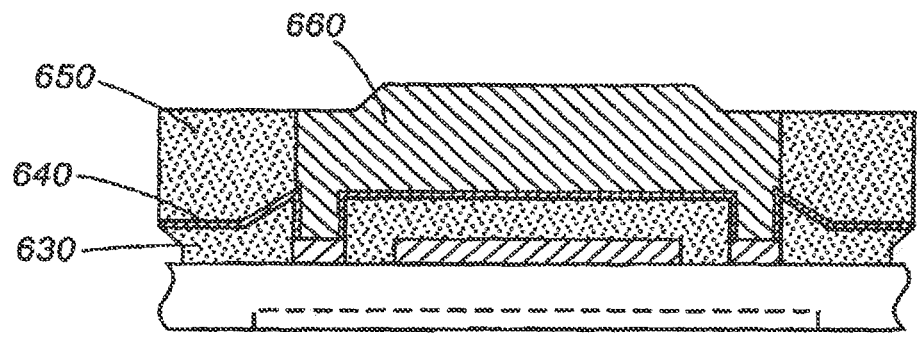
FIG. 20 is a schematic view showing a fourth step in the manufacturing process of the wireless pressure sensor of FIG. 16.

Referring now to FIG. 20, a second layer 650 of photo definable polymer (the second polymer layer) is deposited and patterned using photolithography. During this process, selected regions are removed from the surface of the substrate, defining new windows 652 (large openings) in the second polymer layer 650 without affecting any other previously deposited layer (especially the first polymer layer 630). The in-plane geometry of the new windows represents the in-plane geometry of the top electrode 606 (FIG. 17). The geometry of the new windows extends to encompass the geometry and location of the anchor sites 612.

Regions where the photo definable polymer has been removed are subjected to a method known as electroplating. In that fashion, metals like copper or gold can grow and adhere in the presence of the seed layer. The electroplating occurs at the same time at the anchoring sites, on the sidewalls, and on any other region exposed through windows opened in the second polymer layer. The resulting structure is a continuous electroplated film 660 of the desired thickness. The thickness can range from few micrometers to few tens of micrometers. Electroplated copper is preferred for its ease of deposition and low cost.

Figure 21:
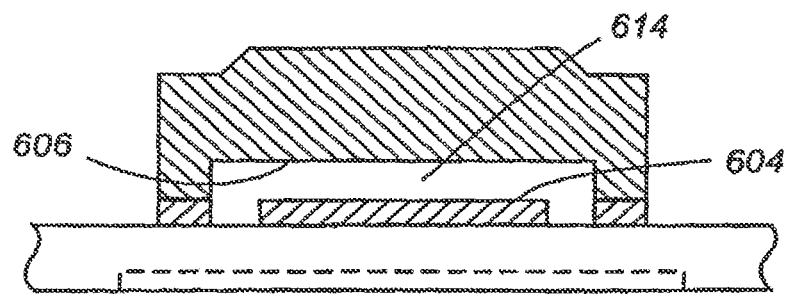
FIG. 21 is a schematic view showing a fifth step in the manufacturing process of the wireless pressure sensor of FIG. 16.

Next, as shown in FIG. 21 the second polymer layer 650, the metal layer 640, and the sacrificial layer 630 are removed using wet or dry selective removal techniques. The preferred removal technique for both the second polymer layer 650 and the sacrificial layer 630 is wet dissolution in appropriate solvents such as acetone. At this point, both bottom and top plates 604, 606 are formed. The top plate 606 is suspended above the bottom plate 604 and separated from it by an air gap 614, which corresponds to the thickness of the first polymer layer.

As the fabrication of the sensor continues, the coil 616 is bunt or assembled using any of the methods described herein. Its terminals are electrically and mechanically connected to either one of the opposite plates 604, 606 of the capacitor 602. Finally, as shown in FIG. 16, the capsule 618 or other form of hermetic surrounding is assembled onto the wafer 608 to encapsulate the coil 616 and capacitor 602.

A variation on the two-wafer design is shown in FIGS. 24-28. A sensor 700 comprises a thick upper wafer 702 and a thinner lower wafer 704. The thin lower wafer 704 comprises the pressure-sensitive deflective region portion 706 of the sensor 700. A notch 708 is optionally formed in the upper wafer 702 to accommodate an anchor, such as a corkscrew, hook, barb, or other suitable stabilization means. The notch can be created on the backside of the wafer directly if the cap is sufficiently thick to accommodate the notch and a separation distance between the bottom of the notch and the coil body without causing any parasitic, deleterious electromagnetic or mechanical effects on the sensor function. Alternatively, the notch can be created by using wet or dry methods in a separate wafer or plurality of wafers and then bonded to the backside of the sensor. The notch can have a variety of regular or irregular geometries and can have rough or smooth sidewalls—any configuration achievable by conventional technologies that would impart some advantage or feature to assist in fixing the anchor mechanism to the sensor.

A capacitor 710 comprises a power plate 711 formed on the inner surface of the lower wafer 704 and an opposing pair of upper plates 712, 714 formed on the lower surface of the upper wafer 702. A channel 716 is formed in the upper wafer 702 to receive an inductor coil 718. The inductor coil 718 includes leads 720 that conductively connect the opposite ends of the coil to the upper plates 712, 714.

Figure 25:
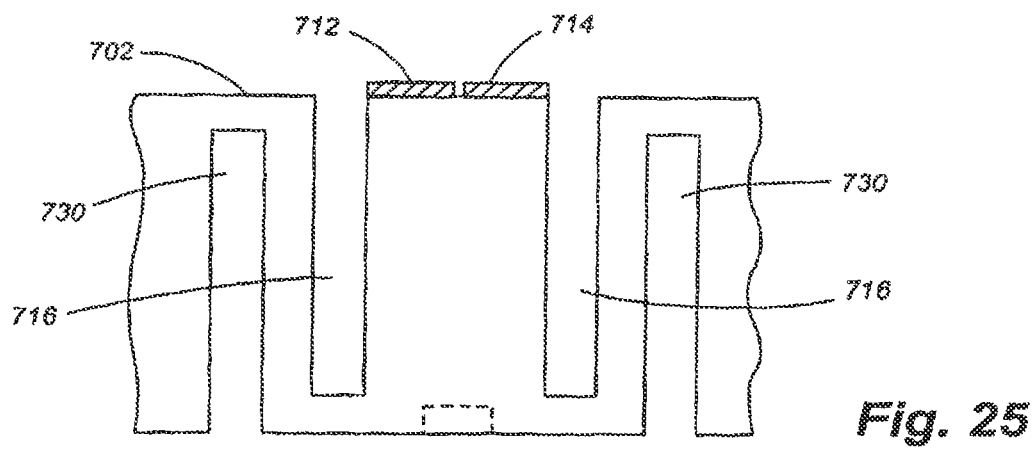
FIG. 25 is a schematic view showing a first step in the manufacturing process of the wireless pressure sensor of FIG. 24.

Manufacture of the sensor 700 will be explained with reference to FIGS. 25-28. Referring first to FIG. 25, a dicing trench 730 is formed in the lower portion of the upper wafer 702 (shown inverted for the manufacturing process). The dicing trench 730 is a feature, which comprises a reduction in thickness of the wafer 702 along a line that defines the perimeter of the sensor 700. The dicing trench 730 is advantageous where reduction of the amount of energy transferred to the sensor during dicing is needed, for example, to protect the sensor from heat damage when dicing with a laser. When the wafer thickness is reduced, less energy is required to cut the sensor from the rest of the wafer, and thus less thermal energy is transferred to the critical components of the sensor.

As can also be seen in FIG. 25, the channel 716 is formed in the upper surface of the upper wafer 702. The lower capacitor plates 712, 714 are formed on the upper surface of the upper wafer 702.

Figure 24:
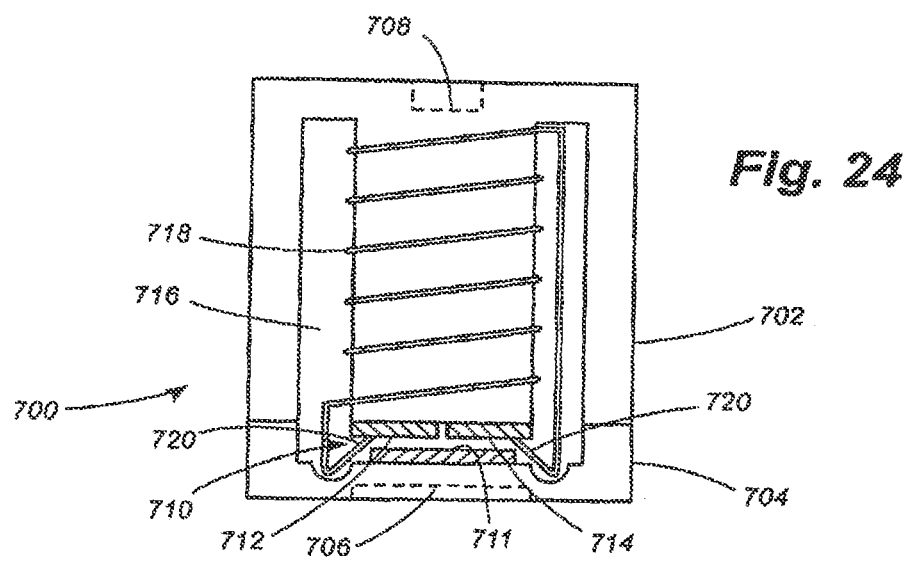
FIG. 24 is a schematic view of another embodiment of a wireless pressure sensor in which the pressure sensitive capacitor and three-dimensional inductor coil are formed on two wafers.
Figure 26:
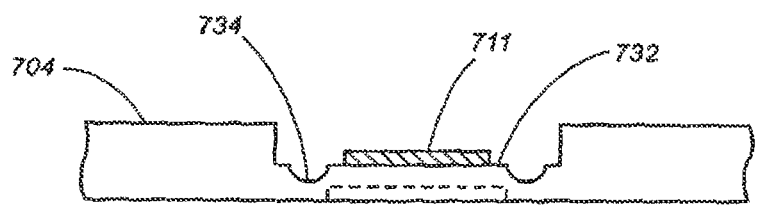
FIG. 26 is a schematic view showing a second step in the manufacturing process of the wireless pressure sensor of FIG. 24.

Referring now to FIG. 26, a recess 732 is formed in the upper surface of the lower wafer 704. The recess optionally includes troughs 734 for providing clearance for the leads 720 of the inductor coil 718 (FIG. 24). The lower capacitor plate 711 is formed in the base of the recess 732 in the upper surface of the lower wafer 704.

Figure 27:
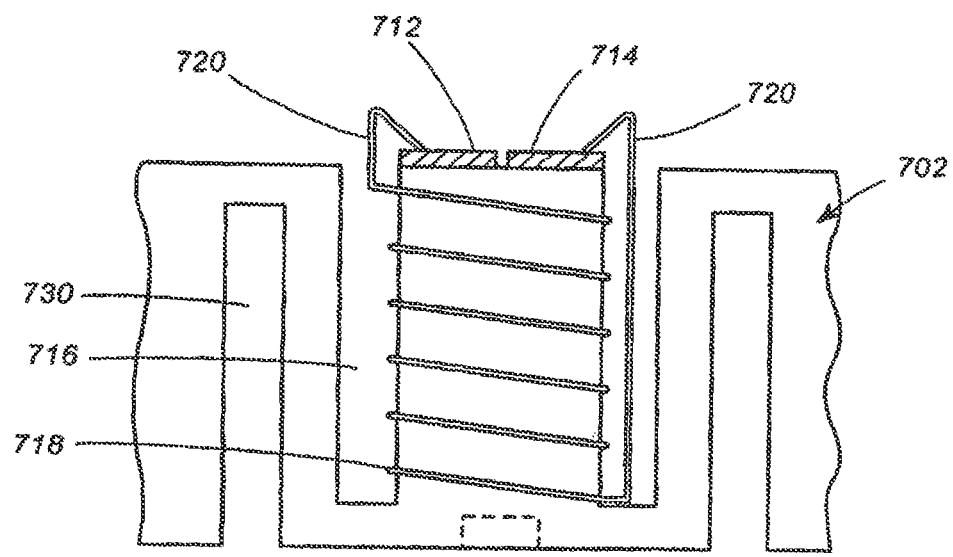
FIG. 27 is a schematic view showing a third step in the manufacturing process of the wireless pressure sensor of FIG. 24.

Referring now to FIG. 27, the inductor coil 718 is introduced into the annular recess 716 of the upper wafer 702. The two leads 720 of the inductor coil 718 are connected to the upper capacitor plates 712, 714.

Figure 28:
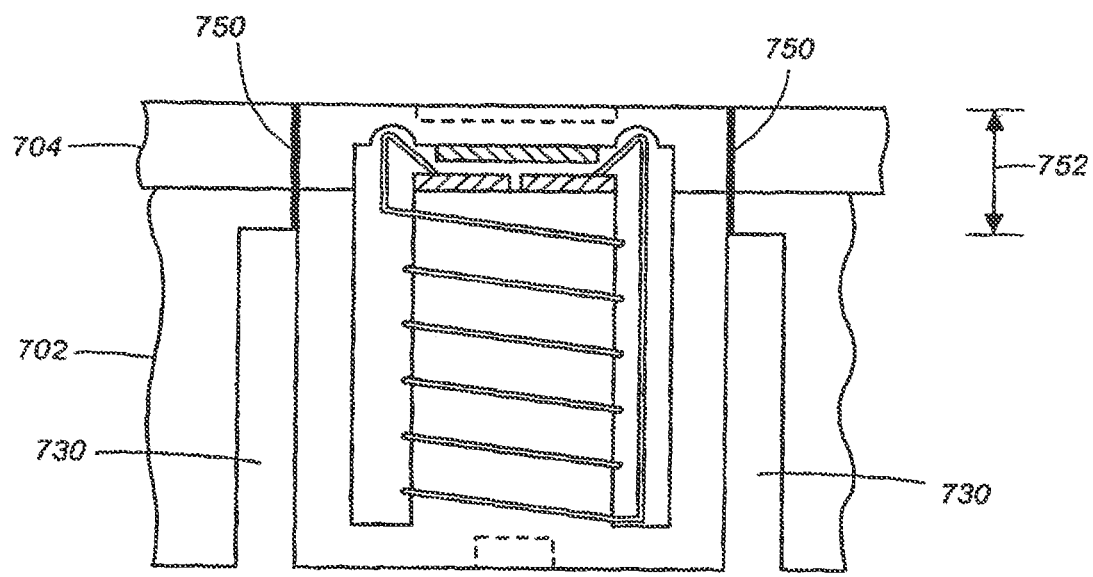
FIG. 28 is a schematic view showing a fourth step in the manufacturing process of the wireless pressure sensor of FIG. 24.
Figure 29:
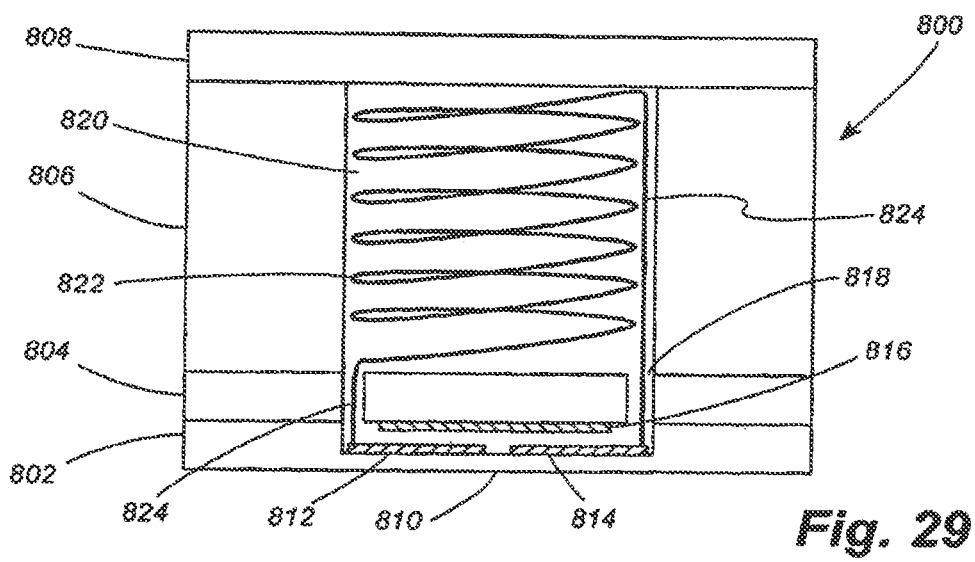
FIG. 29 is a schematic view of an embodiment of a wireless pressure sensor utilizing four wafers.

Referring to FIG. 28, the lower wafer 704 is now inverted and positioned atop the upper wafer 702. A laser is then used to cut and simultaneously heat bond the wafers 702, 704 at the lines 750 to complete fabrication of the sensor 700. Because of the presence of the dicing trenches 730, the laser need cut through only a thickness corresponding to the double arrow 752. This shallow cut minimizes the amount of thermal energy transferred to the internal components of the sensor.

FIGS. 29-32 depict an embodiment of a sensor 800 manufactured from four stacked wafers, 802, 804, 806, and 808. The bottom wafer 802 comprises the pressure-sensitive deflective region 810 and a pair of capacitor plates 812, 814 formed on its upper surface. The second wafer 804 comprises a capacitor plate 816 formed on its lower surface and a pair of through-holes 818 for electrical connections. The third wafer 806 comprises a cylindrical cavity 820 for accommodating an inductance coil 822. Leads 824 of the inductance coil 822 extend through the holes 818 in the second wafer 804 and connect to the capacitor plates 812, 814. The fourth wafer 808 fits atop the third wafer to provide a sealed structure.

Figure 30:
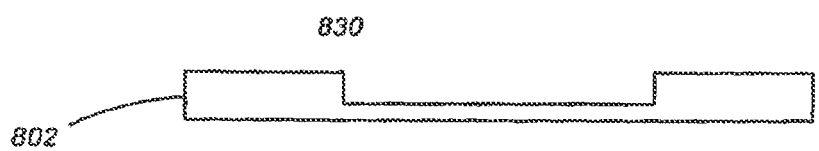
FIG. 30 is a schematic view showing a first step in the manufacturing process of the wireless pressure sensor of FIG. 29.
Figure 31:
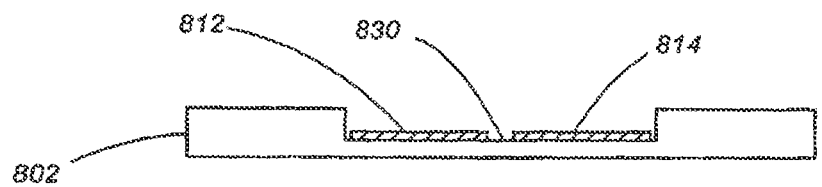
FIG. 31 is a schematic view showing a second step in the manufacturing process of the wireless pressure sensor of FIG. 29.
Figure 32:
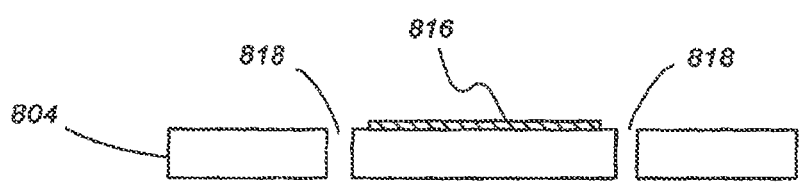
FIG. 32 is a schematic view showing a third step in the manufacturing process of the wireless pressure sensor of FIG. 29.
Figure 33:
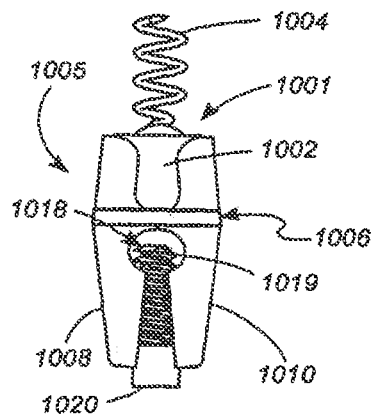
FIG. 33 is a side view of a pressure sensor and a retention mechanism of a delivery device, with the retention mechanism in a closed configuration.
Figure 34:
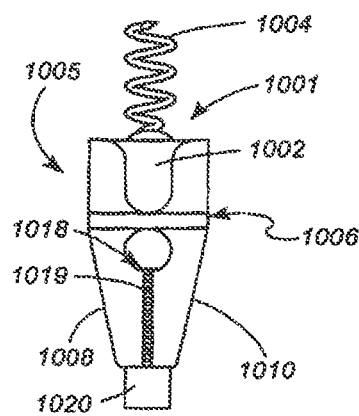
FIG. 34 is a side view of the pressure sensor and retention mechanism FIG. 33, with the retention mechanism in an open configuration.
Figure 35:
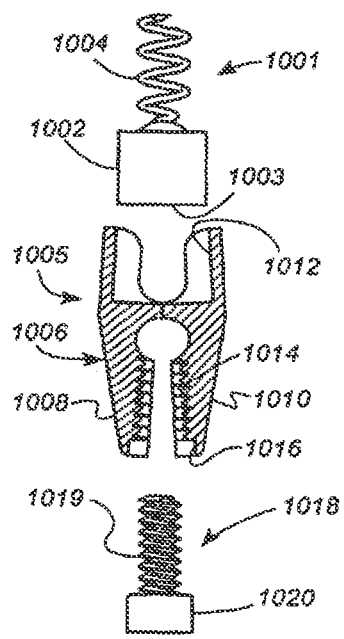
FIG. 35 is a side view of the pressure sensor and retention mechanism FIG. 33, with the retention mechanism in a closed configuration and shown in cross-section.
Figure 36:
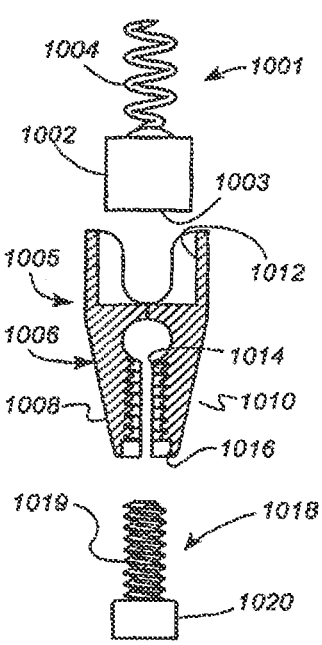
FIG. 36 is a side view of the pressure sensor and retention mechanism FIG. 33, with the retention mechanism in an open configuration and shown in cross-section.
Figure 37:
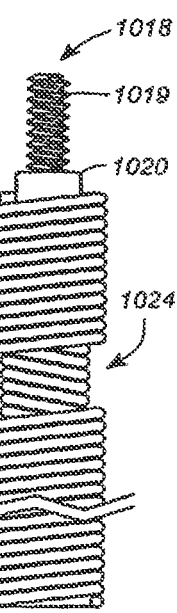
FIG. 37 is a side view of a dual-coil shaft of a delivery device, with a portion of the outer coil being removed to show the inner coil.

FIG. 30 illustrates a first step in the process for manufacturing the sensor 800. A recess 830 is formed in the upper surface of the bottom wafer. Then, as shown in FIG. 32, the plates 812, 814 are formed in the base of the recess 830. Referring to FIG. 32, the plate 816 is formed on the upper surface of the second wafer 804, and the through holes 818 are formed at the periphery of the plate 816. The second wafer is then inverted and stacked on top of the first wafer.

Thereafter, the coil 822 is positioned atop the second wafer, and electrical connections are made through the holes 818 to the lower plates 812, 814. After formation of the pressure sensitive, capacitor and inductor coil and connecting them together, hermetic encapsulation of the pressure sensitive cavity and inductor coil is performed. The third substrate wafer 806 is prepared with the deep recess 820, sufficient to contain the inductor coil 822. The recess 820 can be formed in a variety of ways, including laser rastering, glass machining, and ultrasonic machining. This third wafer 806 is bonded to the second wafer 804 and subsequently, the sensors are cut out using a laser to release the sensors from the wafer stack and form the hermetic seal in the process of the cut.

The sensors described above can be adapted for use within an organ or a lumen, depending upon what type of attachment or stabilizing means is employed. FIGS. 33-36 illustrate a sensor 1001 suitable for use within an organ such as the heart. The sensor 1001 has a generally cylindrical body 1002 that hermetically houses the capacitor and inductor elements previously described. The sensor 1001 further has a pressure sensitive surface 1003 (FIGS. 35 and 36) on one end of the cylindrical body 1002 and a screw-type anchoring device 1004 extending upward from the opposite end of the body.

FIGS. 33-41 illustrate a first embodiment of a delivery device 1000 (FIGS. 38, 40, and 41) for implanting a pressure sensor 1001 in a heart chamber. The sensor 1001 has a generally cylindrical body 1002 that houses the capacitor and inductor elements previously described. The sensor 1001 further has a pressure sensitive surface 1003 (FIGS. 35, 36, and 41) on one end of the cylindrical body 1002 and a screw-type anchoring device 1004 extending upward from the opposite end of the body. A retention mechanism 1005 of the delivery device 1000 comprises a "clamshell" housing 1006 wherein left and right housing halves 1008, 1010 are resiliently deformable with respect to one another, much in the manner of a clothespin. The housing 1006 has a recess 1012 (FIGS. 35 and 36) formed in its upper end, dimensioned to receive the sensor 1001 therewithin. A reverse-threaded bore 1014 is formed in the lower end of the housing 1006, and a smooth counterbore 1016 is formed in the lower end of the housing 1006 coaxially with the threaded bore 1014.

With further reference to the delivery device 1000, a screw 1018 has a reverse-threaded shaft 1019 and a screw head 1020. The screw head 1020 is mounted to the upper end of a dual-coil, flexible, torqueable shaft 1022. As can be seen at 1024 of FIG. 37, a portion of the outer coil 1026 is removed for purposes of illustration to show the inner coil 1028, which is counterwound with respect to the outer coil 1026.

The reverse-threaded screw 1018 threadably engages the reverse-threaded bore 1014 in the lower end of the retention mechanism 1005. As the screw head 1020 advances into the smooth counterbore 1016 in the base of the housing 1006, the lower ends of the two housing halves 1008, 1010 are spread apart. This causes the upper ends of the housing halves 1008, 1010 to close together, thereby grasping the sensor 1001.

Referring now to FIGS. 38-41, delivery of the sensor 1001 of the invention to a heart chamber may be accomplished as follows. The physician gains access into a vein that is suitable for access into the right ventricle using methods such as the Seldinger technique. Examples of these access sites would be the right jugular, left subclavian, or right femoral veins. A guidewire is advanced into the right ventricle. A large vessel introducer with an adjustable hemostatic valve is inserted over the guidewire and advanced until its tip is positioned in the right ventricle.

The sensor 1001 is mounted to the delivery device 1000 with the longitudinal axis of the device oriented normal to the pressure-sensitive surface of the sensor and with the anchor or stabilizer 1004 facing the distal end of the shaft 1022. The sensor anchor 1004 can be covered with a soluble, biocompatible material, or a thin, retractable diaphragm cover (not shown). The purpose of such covering is to conceal the anchoring mechanism or stabilizer 1004 and to protect the heart from inadvertent damage during sensor positioning prior to engaging the anchoring mechanism (which, in the case of the disclosed sensor 1001 is configured to engage the tissue of the septum). A torqueable, kink-resistant, shaped guiding catheter (not shown) can be loaded over the shaft 1022 of the delivery device in order to provide additional means for steering the sensor into position. The characteristics of this guiding catheter are that the outer diameter is small enough to fit within the introducer sheath, and the inner diameter is large enough to load over the shaft 1022 of the delivery device 1000.

Figure 38:
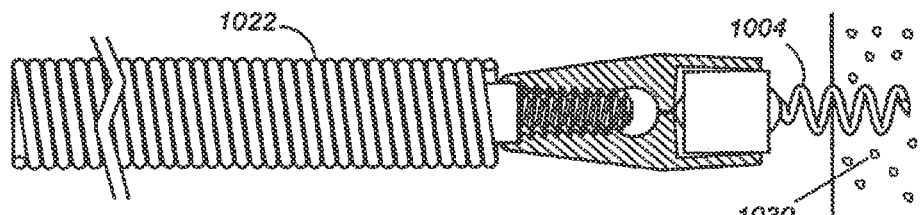
FIG. 38 is a side view of a delivery device comprising the retention mechanism of FIG. 33 and the shaft of FIG. 37, illustrating a first step in the delivery of a sensor into the wall of a septum.
Figure 39:
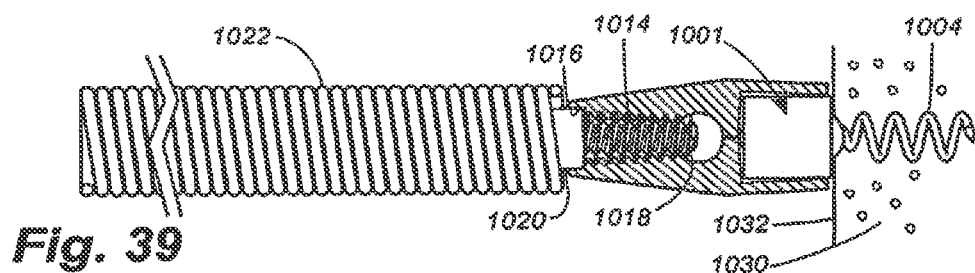
FIG. 39 is a side view of the delivery device of FIG. 38, illustrating a second step in the delivery of a sensor into the wall of a septum.
Figure 40:
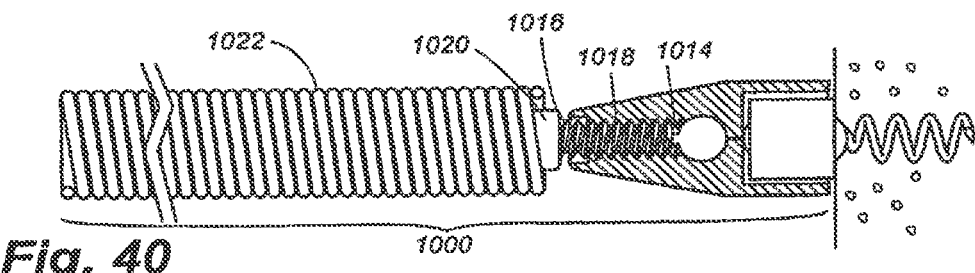
FIG. 40 is a side view of the delivery device of FIG. 38, illustrating a third step in the delivery of a sensor into the wall of a septum.
Figure 41:
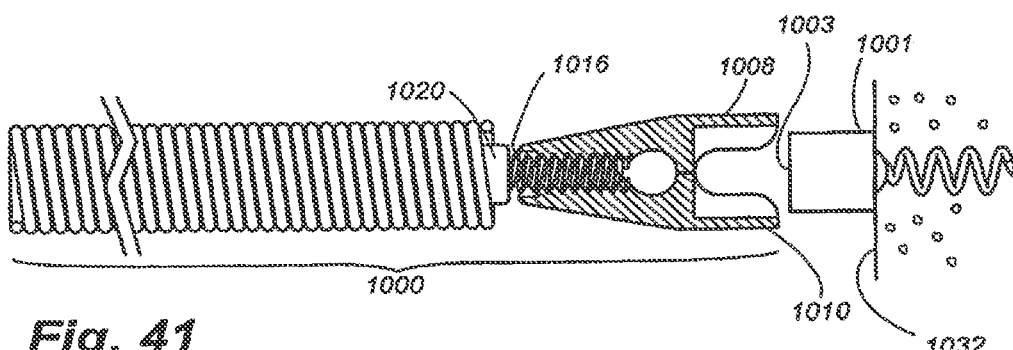
FIG. 41 is a side view of the delivery device of FIG. 38, illustrating a fourth step in the delivery of a sensor into the wall of a septum.

Referring to FIG. 38, the shaft 1022 of the delivery device 1000 is rotated in a clockwise direction to screw the anchor 1004 of the sensor into the tissue 1030 of the septum. When the anchor 1004 has been fully inserted into the tissue 1030, as shown in FIG. 39, the sensor 1001 tightens against the wall 1032 of the septum and creates a resistance. This resistance is sufficient to overcome the resistance between the reverse-threaded screw 1018 and the corresponding reverse-threaded bore 1014 in the housing 1006 of the retention mechanism 1005. Consequently, continued rotation of the shaft 1022 of the delivery device 1000 in the clockwise direction will withdraw the screw 1018 from its bore 1014, as illustrated in FIG. 40. Once the screw head 1020 has cleared the smooth counterbore 1016 in the lower end of the housing 1006 of the retention mechanism, the lower ends of the two housing halves 1008, 1010 return to their normal, closed configuration, thereby opening the upper ends of the two housing halves and releasing the sensor 1001, as depicted in FIG. 41. The delivery device 1000 is then withdrawn from the patient, leaving the sensor 1001 anchored to the wall 1032 of the septum with its pressure-sensing surface 1003 facing outward.

A feature of the disclosed embodiment is the use of a reverse-threaded screw 1018 and corresponding bore 1014 so that rotating the shaft 1022 in a normal "tightening" direction will first screw the sensor into the wall of the septum and then open the retention mechanism 1005 to release the sensor 1001, all without having to reverse direction of rotation of the shaft. To permit this arrangement, it is necessary that the screw 1018 engage the retention mechanism 1005 with enough mechanical force that the initial rotation of the shaft 1022 will cause the sensor to screw into the wall of the septum, rather than withdraw the screw 1018 from the retention mechanism 1005. In addition, it is also necessary that the screw be sufficiently loose with respect to the retention mechanism that once the sensor has completely screwed into the wall of the septum, the torque resistance will overcome the engagement between the screw and the retention mechanism rather than continue to rotate the sensor 1001. This feature can be accomplished, for example, by controlling the tolerances between the screw 1018 and the retention mechanism 1005, and by controlling the resilient force exerted by the housing 1006 against the head 1020 of the screw.

Figure 42:
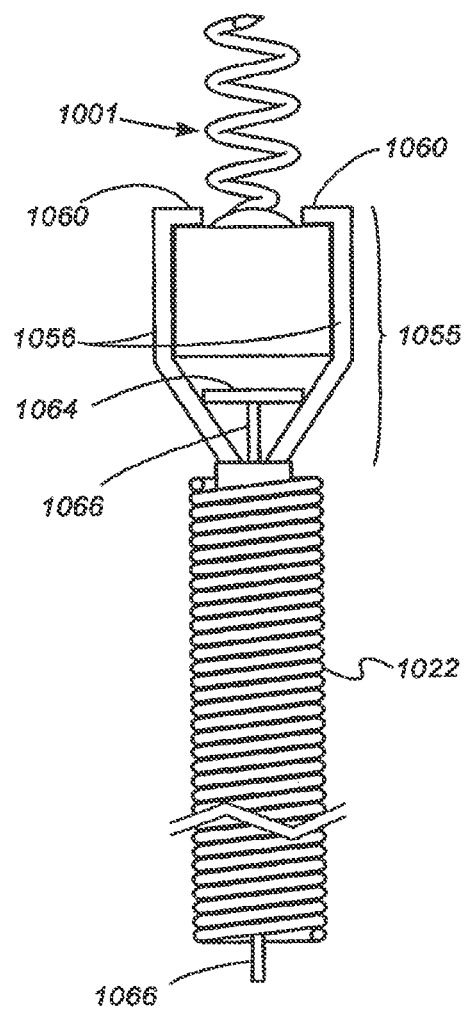
FIG. 42 is a side view of an alternate embodiment of a delivery device for delivering a sensor into the wall of a septum, with the retention mechanism of the delivery device in a closed configuration.
Figure 43:
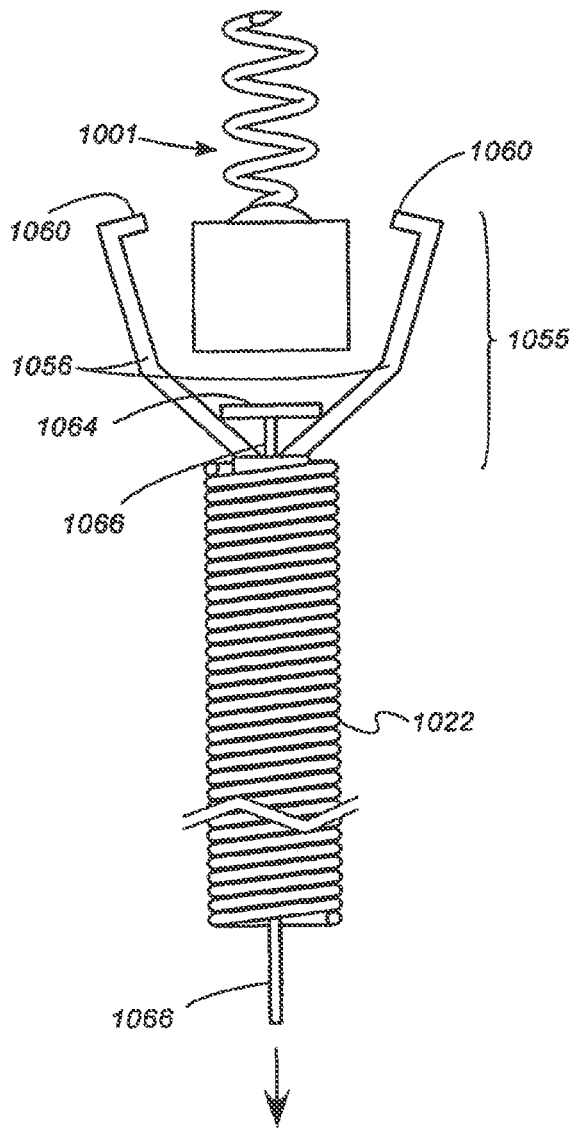
FIG. 43 is a side view of the delivery device of FIG. 42 showing the retention mechanism in an open configuration.

FIGS. 42 and 43 illustrate an alternate embodiment of a retention mechanism 1055. The retention mechanism 1055 is mounted to a flexible, torqueable shaft 1022, just as in the previously disclosed embodiment. However, rather than the clamshell housing 1006, the retention mechanism 1055 comprises a plurality of resilient wire fingers 1056 extending upward from a base 1058. The fingers 1056 of the disclosed embodiment are comprised of nitinol, though any suitable resilient biocompatible material can be used. Hooks 1060 at the upper ends of the wire fingers 1056 wrap around the upper edges of the body 1002 of the sensor 1001. In the disclosed embodiment there are four such wire fingers 1056 spaced 90.degree. apart around the circumference of the cylindrical sensor body 1002, although a greater or lesser number of fingers 1056 can be used. Only two fingers 1056 are shown in the drawings for convenience of illustration.

A spreader 1064 is disposed between the fingers 1056. The spreader 1064 is attached to a pull-wire 1066, which extends through the longitudinal opening of the shaft 1022 and to a location outside of the patient. When the physician desires to release the retention mechanism 1055 from the sensor 1001, he simply exerts a tension on the pull-wire 1066. In response, the spreader moves downward and biases the fingers 1056 apart, releasing the sensor 1001 from the retention mechanism 1055. In the disclosed embodiment the spreader 1064 is a circular disk or a frustocone, but it will be understood that any shape can be used which biases the fingers apart in response to tension applied to the pull-wire 1066.

Figure 44:
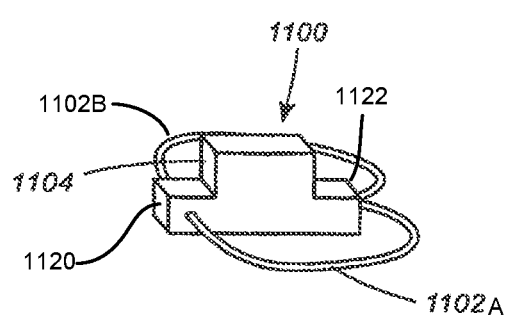
FIG. 44 is an isometric view of a sensor comprising an alternate arrangement for anchoring the sensor within a lumen of a patient.
Figure 45:
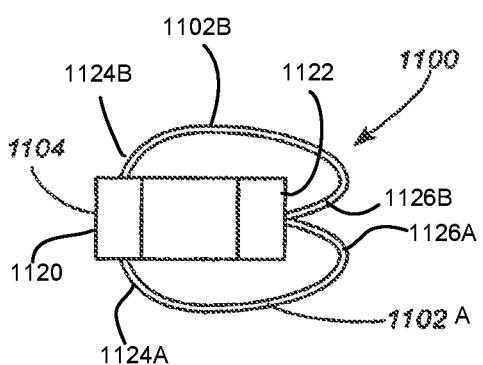
FIG. 45 is a top view of the sensor of FIG. 44.
Figure 46:
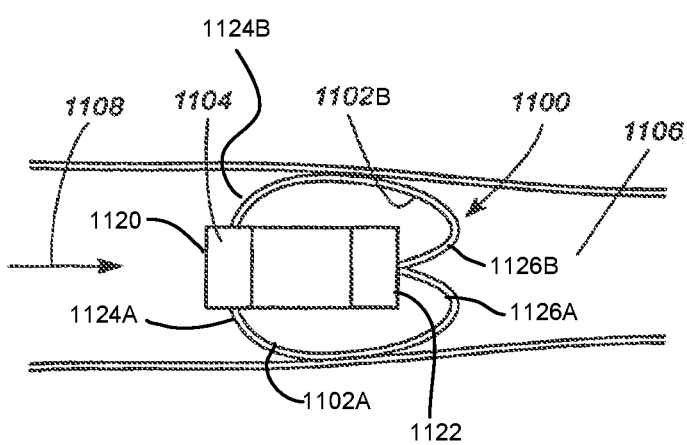
FIG. 46 is a top view showing the sensor of FIG. 44 lodged within a lumen.

By changing the anchoring means, the same basic sensor 1001 can be adapted for use within a lumen such as an artery or arteriole in the pulmonary artery vasculature. FIGS. 44-46 illustrate a sensor 1100 of the type described above. The sensor 1100 has a sensor body 1104 with a proximal end 1120 and a distal end 1122. First and second anchoring elements 1102A, 1102B are provided as wire loops extending outward from the sensor body 1104. The first anchoring element 1102A has a first end 1124A coupled to the proximal end 1120 of the sensor body 1104. The first anchoring element 1102A has a second end 1126A coupled to the distal end 1122 of the sensor body 1104. The second anchoring element 1102B has a first end 1124B coupled to the proximal end 1120 of the sensor body 1104. The second anchoring element 1102B has a second end 1126B coupled to the distal end 1122 of the sensor body 1104. As shown in FIG. 46, the wire loop 1102 causes the sensor 1100 to lodge within a lumen 1106, with the sensor located centrally within the lumen and allowing blood flow all around in the direction indicated by the arrow 1108.

A delivery apparatus for securing, delivering and deploying an implant 1100 having an anchoring mechanism 1102 is shown in FIGS. 47-51. The various components of the delivery apparatus are shown individually in FIGS. 47-50. As shown in FIG. 47, the delivery apparatus includes an elongated shaft 1152 having proximal and distal ends 1153, 1154 respectively. The shaft 1152 has a main lumen 1155, which extends the length of the shaft. A port 1156 places the main lumen 1155 in communication with the ambient at an Intermediate location along the shaft 1152. A secondary lumen includes a proximal portion 1158 and a distal portion 1159. The proximal portion 1158 extends along a partial length of the shaft 1152 and terminates in a port 1160 in the sidewall of the shaft. The distal portion 1159 originates in a port 1161 in the sidewall of the shaft and extends in a distal direction to an end.

A tether wire, 1163 shown in FIG. 48, is adapted to be slidably positioned within the secondary lumen of the shaft 1152.

A core wire 1164, shown in FIG. 49, is configured to be received within the main lumen 1155 of the shaft 1152 and provides stiffness to the delivery apparatus. The core wire 1164 has a decreasing diameter toward its distal end 1165, providing an increased flexibility in the distal end of the delivery apparatus. The core wire 1164 is fixed in the main lumen 1155 of the shaft 1152 using adhesive, thermocompression, or any other suitable fixation means.

Referring to FIG. 50, a conventional guide wire 1166 is dimensioned to extend beyond the distal end 1154 of the shaft 1152 and to be received within a distal portion of the main lumen 1155 of the shaft.

FIG. 51 shows the delivery apparatus with sensor 1100 mounted. The core wire 1164 is disposed within the main lumen 1155 of the shaft 1152. The tether wire 1163 extends through the proximal portion 1158 of the secondary lumen of the shaft 1152 and exits through the port 1160 in the shaft sidewall. The tether wire 1163 then is threaded through the body 1104 of the sensor 1100 and passed into the port 1161 and hence into the distal portion 1159 of the secondary lumen. The guidewire 1166 extends alongside the proximal portion of the shaft 1152 and enters the main lumen 1155 of the shaft 1152 at the port 1156. The guidewire 1166 then passes through the distal portion of the main lumen 1155 and exits the distal end 1154 of the shaft 1152.

A vessel introducer is placed in an access site such as the right internal jugular vein, the subclavian artery, the right femoral vein, or any other suitable access site. The guidewire 1166 is inserted through the vessel introducer and guided to the target site using suitable medical imaging technology. The delivery apparatus with sensor 1100 mounted thereto is then threaded over the guidewire and inserted into the vessel introducer.

After the delivery apparatus is in the vessel introducer, the apparatus is navigated over the guidewire to a deployment site in the pulmonary artery. The implant 1100 is deployed by pulling the tether wire 1163 proximally to disengage the implant from the shaft 1152. The delivery apparatus and guidewire are then removed from the body.

The implant 1100 may then "float" through the narrowing pulmonary artery vasculature until it reaches a location at which the vessel is sufficiently narrow that the implant lodges within the vessel, as shown in FIG. 46. At that point the implant will be firmly anchored within the vasculature.

In alternate embodiments (not shown), the secondary lumen of the shaft introducer 1150 can comprise a single, uninterrupted lumen having two ports 1160, 1161, rather than two separate lumen portions 1158, 1159. In addition, the secondary lumen can extend all the way through the distal end of the shaft, rather than terminating at an end short of the distal end of the shaft.

Interrogation System

Embodiments are directed towards a system and method for communicating with a wireless sensor. Briefly described, the systems and methods determines the resonant frequency of the sensor by adjusting the phase and frequency of an energizing signal until the frequency of this signal locks to the resonant frequency of the sensor. The system energizes the sensor with a low duty cycle, gated burst of RF energy of a predetermined frequency or set of frequencies and predetermined amplitude. This signal induces a current in the sensor that can be used to track the resonant frequency of the sensor. The system receives the ring down response of the sensor and determines the resonant frequency of the sensor, which is used to calculate the measured physical parameter. The system uses a pair of phase locked loops ("PLL"s) to adjust the phase and the frequency of the energizing signal to track the resonant frequency of the sensor.

Exemplary System

Figure 52:
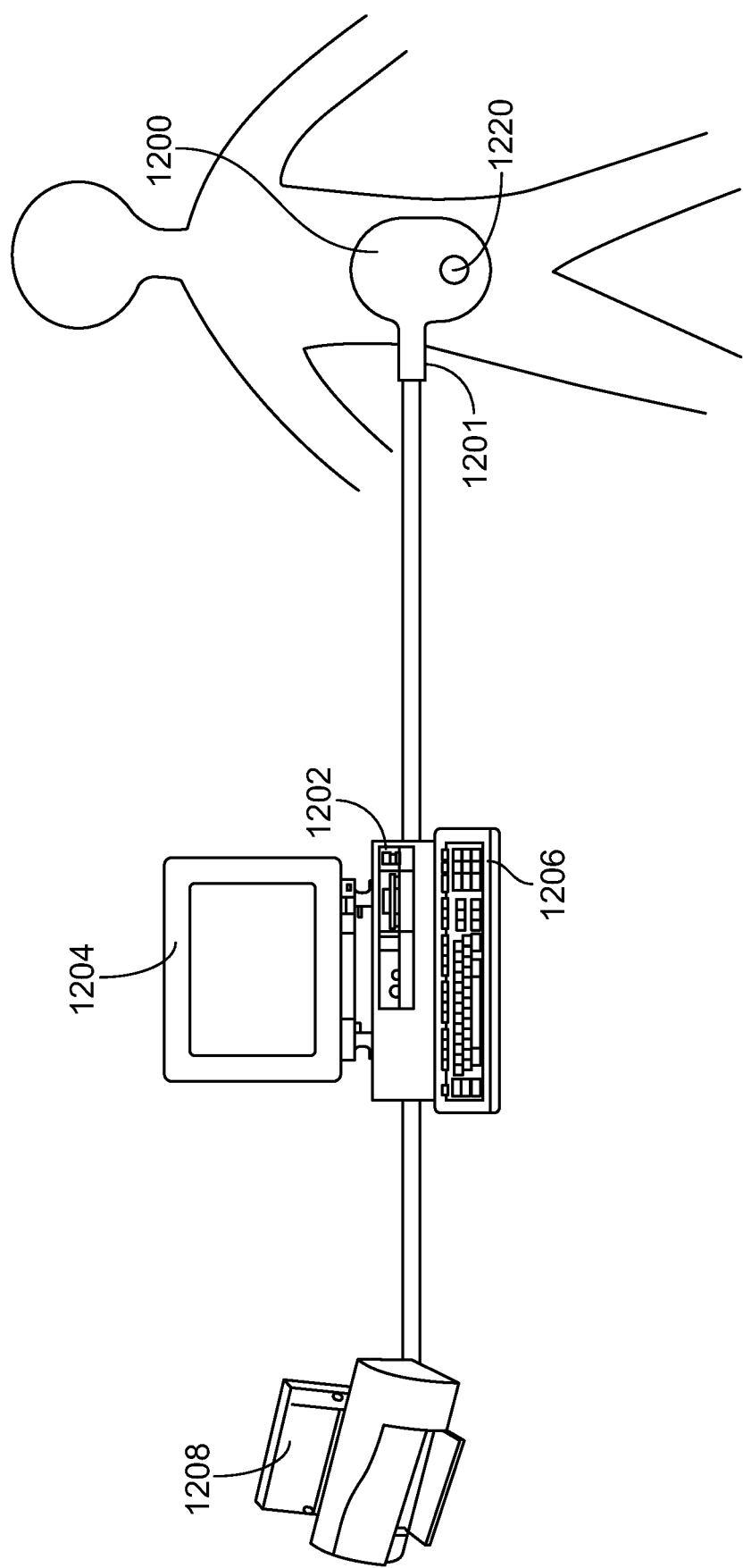
FIG. 52 is a block diagram of an exemplary system for communicating with a wireless sensor in accordance with an embodiment of the invention.

FIG. 52 illustrates an exemplary system for communicating with a wireless sensor implanted within a body. The system includes a coupling loop 1200, a base unit 1202, a display device 1204 and an input device 1206, such as a keyboard.

The coupling loop is formed from a band of copper. In one embodiment, the loop is eight inches in diameter. The coupling loop includes switching and filtering circuitry that is enclosed within a shielded box 1201. The loop charges the sensor and then couples signals from the sensor into the receiver. The antenna can be shielded to attenuate in-band noise and electromagnetic emissions.

Figure 58:
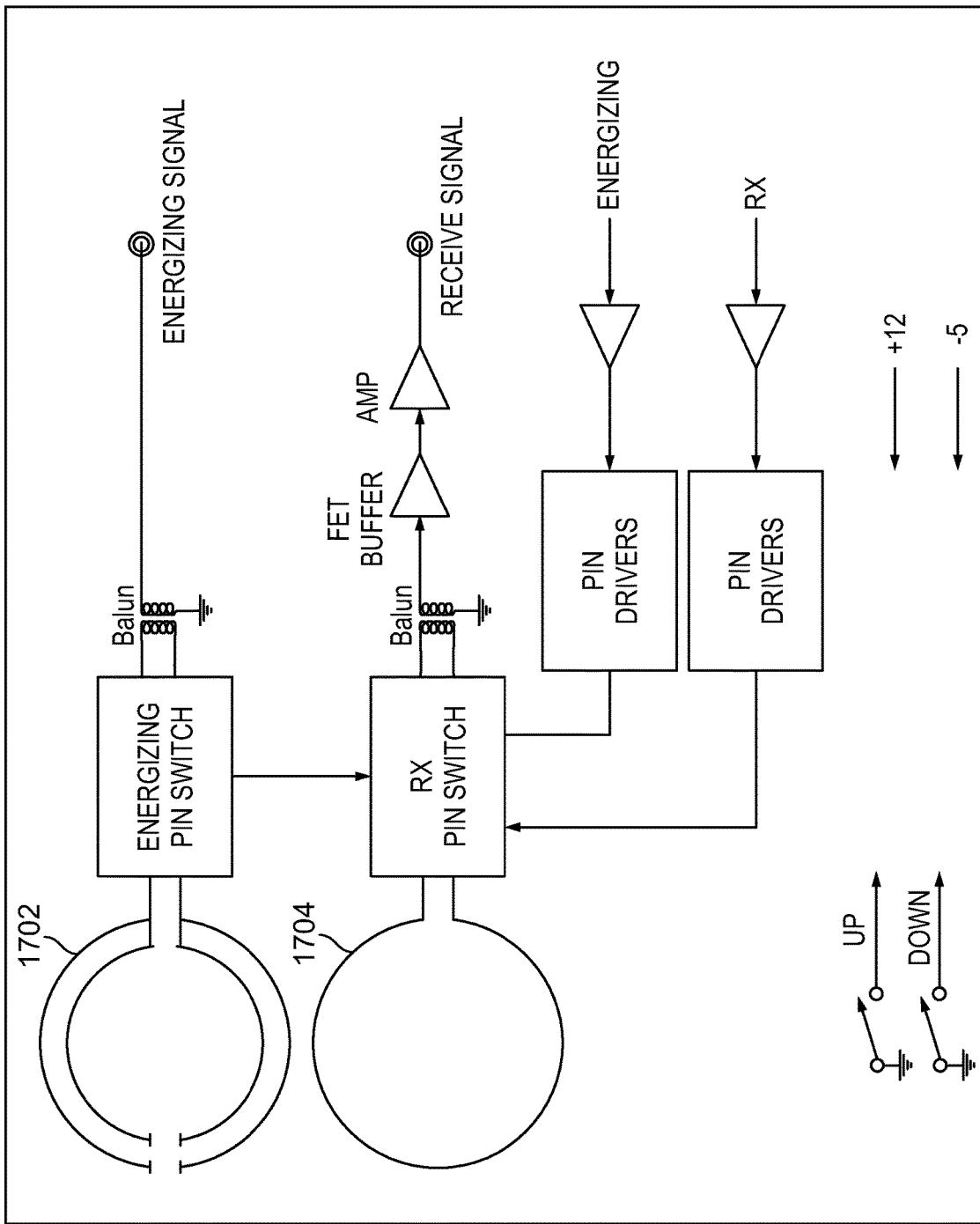
FIG. 58 illustrates a coupling loop in accordance with an embodiment of the invention.

Another possible embodiment for a coupling loop is shown in FIG. 58, which shows separate loops for energizing 1702 and for receiving 1704, although a single loop can be used for both functions. PIN diode switching inside the loop assembly is used to provide isolation between the energizing phase and the receive phase by opening the RX path pin diodes during the energizing period, and opening the energizing path pin diodes during the coupling period. Multiple energizing loops can be staggered tuned to achieve a wider bandwidth of matching between the transmit coils and the transmit circuitry.

The base unit includes an RF amplifier, a receiver, and signal processing circuitry. Additional details of the circuitry are described below in connection with FIG. 54.

The display 1204 and the input device 1206 are used in connection with the user interface for the system. In the embodiment illustrated in FIG. 52 the display device and the input device are connected to the base unit. In this embodiment, the base unit also provides conventional computing functions. In other embodiments, the base unit can be connected to a conventional computer, such as a laptop, via a communications link, such as an RS-232 link. If a separate computer is used, then the display device and the input devices associated with the computer can be used to provide the user interface. In one embodiment, LABVIEW software is used to provide the user interface, as well as to provide graphics, store and organize data and perform calculations for calibration and normalization. The user interface records and displays patient data and guides the user through surgical and follow-up procedures.

An optional printer 1208 is connected to the base unit and can be used to print out patient data or other types of information. As will be apparent to those skilled in the art other configurations of the system, as well as additional or fewer components can be utilized with the invention.

Patient and system information can be stored within a removable data storage unit, such as a portable USB storage device, floppy disk, smart card, or any other similar device. The patient information can be transferred to the physician's personal computer for analysis, review, or storage. An optional network connection can be provided to automate storage or data transfer. Once the data is retrieved from the system, a custom or third party source can be employed to assist the physician with data analysis or storage.

FIG. 53 illustrates the system communicating with a sensor 1220 implanted in a patient. The system is used in two environments: 1) the operating room during implant and 2) the doctor's office during follow-up examinations. During implant the system is used to record at least two measurements. The first measurement is taken during introduction of the sensor for calibration and the second measurement is taken after placement for functional verification. The measurements can be taken by placing the coupling loop either on or adjacent to the patient's back or the patient's stomach for a sensor that measures properties associated with an abdominal aneurysm. For other types of measurements, the coupling loop may be placed in other locations. For example, to measure properties associated with the heart, the coupling loop can be placed on the patient's back or the patient's chest.

The system communicates with the implanted sensor to determine the resonant frequency of the sensor. As described in more detail in the patent documents referenced in the Background section, a sensor typically includes an inductive-capacitive ("LC") resonant circuit having a variable capacitor. The distance between the plates of the variable capacitor varies as the surrounding pressure varies. Thus, the resonant frequency of the circuit can be used to determine the pressure.

Figure 59:
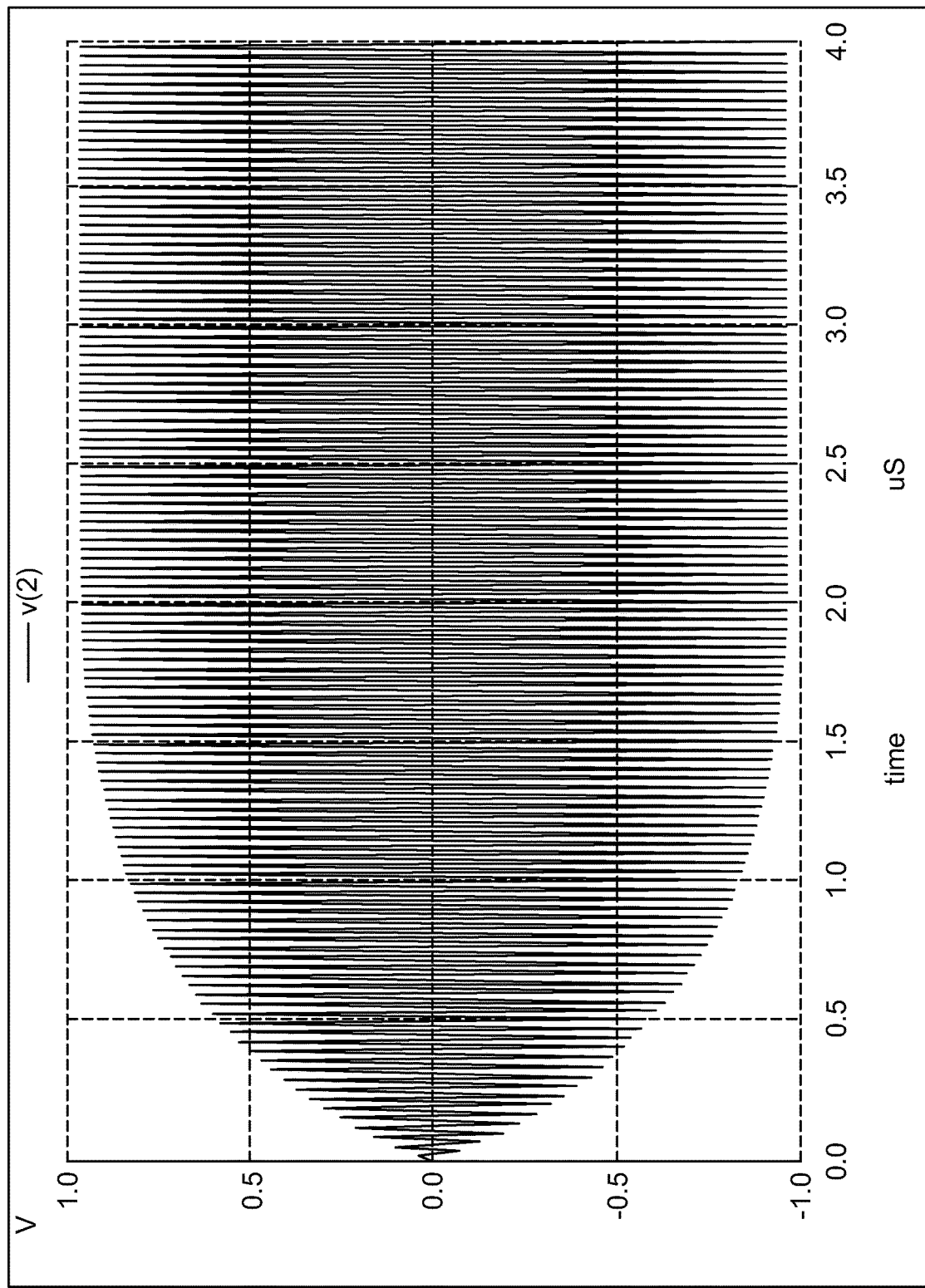
FIG. 59 is a graph illustrating an exemplary charging response of an LC circuit in accordance with an embodiment of the invention.

The system energizes the sensor with an RF burst. The energizing signal is a low duty cycle, gated burst of RF energy of a predetermined frequency or set of frequencies and a predetermined amplitude. Typically, the duty cycle of the energizing signal ranges from 0.1% to 50%. In one embodiment, the system energizes the sensor with a 30-37 MHz fundamental signal at a pulse repetition rate of 100 kHz with a duty cycle of 20%. The energizing signal is coupled to the sensor via a magnetic loop. This signal induces a current in the sensor which has maximum amplitude at the resonant frequency of the sensor. During this time, the sensor charges exponentially to a steady-state amplitude that is proportional to the coupling efficiency, distance between the sensor and loop, and the RF power. FIG. 59 shows the charging response of a typical LC circuit to a burst of RF energy at its resonant frequency. The speed at which the sensor charges is directly related to the Q (quality factor) of the sensor. Therefore, the "on time" of the pulse repetition duty cycle is optimized for the Q of the sensor. The system receives the ring down response of the sensor via magnetic coupling and determines the resonant frequency of the sensor. FIG. 53A illustrates a typical energizing signal and FIGS. 53B, 53C and 53D illustrate typical coupled signals for various values of Q (quality factor) for the sensor. When the main unit is coupling energy at or near the resonant frequency of the sensor, the amplitude of the sensor return is maximized, and the phase of the sensor return will be close to zero degrees with respect to the energizing phase. The sensor return signal is processed via phase-locked-loops to steer the frequency and phase of the next energizing pulse.

Operation of the Base Unit

Figure 54:
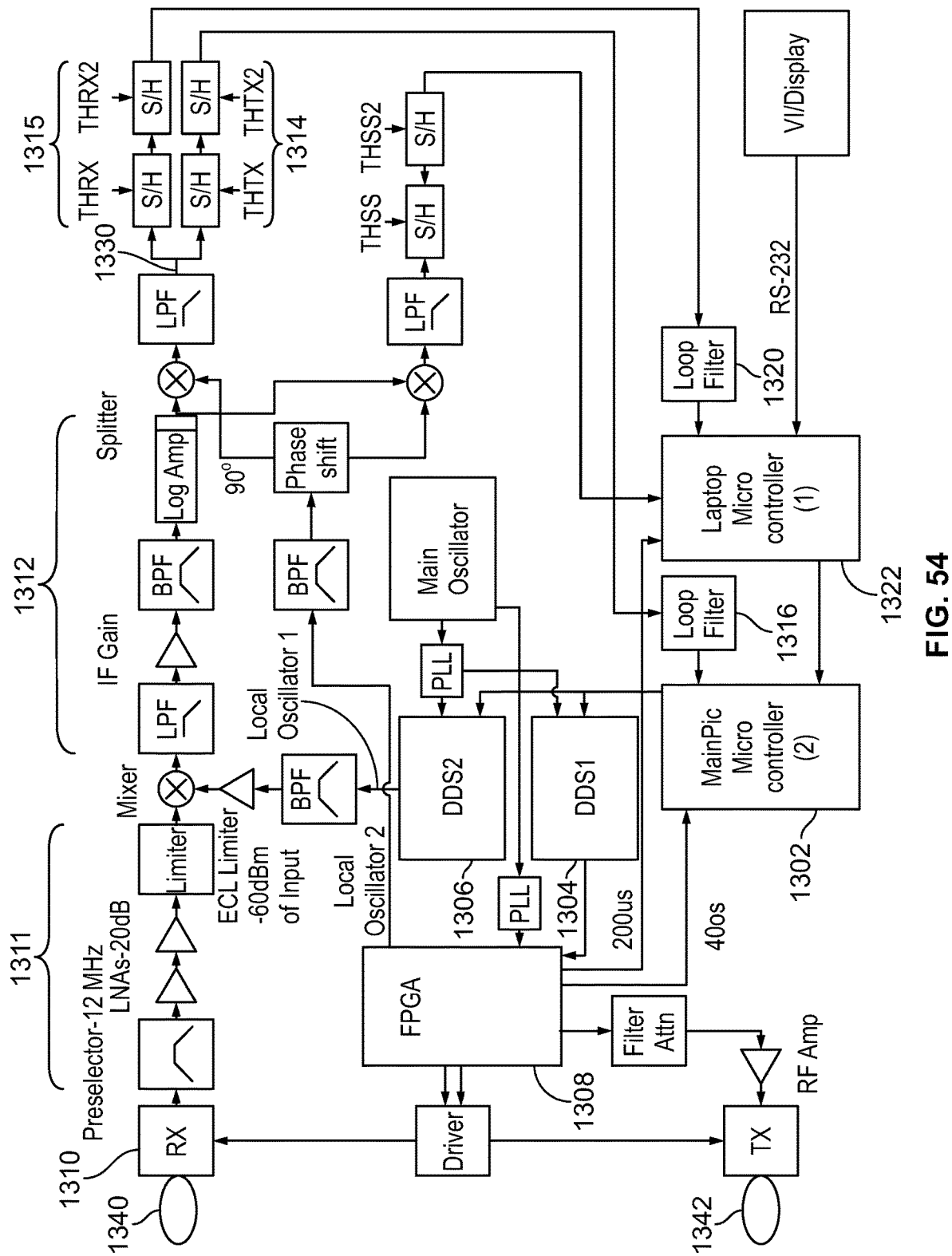
FIG. 54 is a block diagram of an exemplary base unit in accordance with an embodiment of the invention.

FIG. 54 is a block diagram of the signal processing components within an exemplary base unit. The base unit determines the resonant frequency of the sensor by adjusting the energizing signal so that the frequency of the energizing signal matches the resonant frequency of the sensor. In the embodiment illustrated by FIG. 54, two separate processors 1302, 1322 and two separate coupling loops 1340, 1342 are shown. In one embodiment, processor 1302 is associated with the base unit and processor 1322 is associated with a computer connected to the base unit. In other embodiments, a single processor is used that provides the same functions as the two separate processors. In other embodiments a single loop is used for both energizing and for coupling the sensor energy back to the receiver. As will be apparent to those skilled in the art, other configurations of the base unit are possible that use different components.

The embodiment illustrated by FIG. 54 includes a pair of phase lock loops ("PLL"). One of the PLLs is used to adjust the phase of the energizing signal and is referred to herein as the fast PLL. The other PLL is used to adjust the frequency of the energizing signal and is referred to herein as the slow PLL. The base unit provides two cycles: the calibration cycle and the measurement cycle. In one embodiment, the first cycle is a 10 microsecond energizing period for calibration of the system, which is referred to herein as the calibration cycle, and the second cycle is a 10 microsecond energizing/coupling period for energizing the sensor and coupling a return signal from the sensor, which is referred to herein as the measurement cycle. During the calibration cycle, the system generates a calibration signal for system and environmental phase calibration and during the measurement cycle the system both sends and listens for a return signal, i.e. the sensor ring down. Alternatively, as those skilled in the art will appreciate, the calibration cycle and the measurement cycle can be implemented in the same pulse repetition period.

The phase of the energizing signal is adjusted during the calibration cycle by the fast PLL and the frequency of the energizing signal is adjusted during the measurement cycle by the slow PLL. The following description of the operation of the PLLs is presented sequentially for simplicity. However, as those skilled in the art will appreciate, the PLLs actually operate simultaneously.

Initially the frequency of the energizing signal is set to a default value determined by the calibration parameters of the sensor. Each sensor is associated with a number of calibration parameters, such as frequency, offset, and slope. An operator of the system enters the sensor calibration parameters into the system via the user interface and the system determines an initial frequency for the energizing signal based on the particular sensor. Alternatively, the sensor calibration information could be stored on portable storage devices, bar codes, or incorporated within a signal returned from the sensor. The initial phase of the energizing signal is arbitrary.

The initial frequency and the initial phase are communicated from the processor 1302 to the DDSs (direct digital synthesizers) 1304, 1306. The output of DDS1 1304 is set to the initial frequency and initial phase and the output of DDS2 1306 (also referred to as local oscillator 1) is set to the initial frequency plus the frequency of the local oscillator 2. The phase of DDS2 is a fixed constant. In one embodiment, the frequency of local oscillator 2 is 4.725 MHz. The output of DDS1 is gated by the field programmable gate array (FPGA) 1308 to create a pulsed transmit signal having a pulse repetition frequency ("PRF"). The FPGA provides precise gating so that the base unit can sample the receive signal during specific intervals relative to the beginning or end of the calibration cycle.

During the calibration cycle, the calibration signal which enters the receiver 1310 is processed through the receive section 1311 and the IF section 1312, and is sampled. In one embodiment, the calibration signal is the portion of the energizing signal that leaks into the receiver (referred to herein as the energizing leakage signal). The signal is sampled during the on time of the energizing signal by a sample and hold circuit 1314 to determine the phase difference between the signal and local oscillator 2. In the embodiment where the calibration signal is the portion of the energizing signal that leaks into the receiver, the signal is sampled approximately 100 ns after the beginning of the energizing signal pulse. Since the energizing signal is several orders of magnitude greater than the coupled signal, it is assumed that the phase information associated with the leaked signal is due to the energizing signal and the phase delay is due to the circuit elements in the coupling loop, circuit elements in the receiver, and environmental conditions, such as proximity of reflecting objects.

The phase difference is sent to a loop filter 1316. The loop filter is set for the dynamic response of the fast PLL. In one embodiment, the PLL bandwidth is 1000 Hz and the damping ratio is 0.7. A DC offset is added to allow for positive and negative changes. The processor 1302 reads its analog to digital converter (ND) port to receive the phase difference information and adjusts the phase sent to direct digital synthesizer 1 (DDS1) to drive the phase difference to zero. This process is repeated alternatively until the phase difference is zero or another reference phase.

The phase adjustment made during the energizing period acts to zero the phase of the energizing signal with respect to local oscillator 2. Changes in the environment of the antenna or the receive chain impedance, as well as the phase delay within the circuitry prior to sampling affect the phase difference reading and are accommodated by the phase adjustment.

During the measurement cycle, the energizing signal may be blocked from the receiver during the on time of the energizing signal. During the off time of the energizing signal, the receiver is unblocked and the coupled signal from the sensor (referred to herein as the coupled signal or the sensor signal) is received. The coupled signal is amplified and filtered through the receive section 1311. The signal is down converted and additional amplification and filtering takes place in the IF section 1312. In one embodiment, the signal is down converted to 4.725 MHz. After being processed through the IF section, the signal is mixed with local oscillator 2 and sampled by sample and hold circuits 1315 to determine the phase difference between the coupled signal and the energizing signal. In one embodiment, the sampling occurs approximately 30 ns after the energizing signal is turned off.

In other embodiments, group delay or signal amplitude is used to determine the resonant frequency of the sensor. The phase curve of a second order system passes through zero at the resonant frequency. Since the group delay i.e. derivative of the phase curve reaches a maximum at the resonant frequency, the group delay can be used to determine the resonant frequency. Alternatively, the amplitude of the sensor signal can be used to determine the resonant frequency. The sensor acts like a bandpass filter so that the sensor signal reaches a maximum at the resonant frequency.

The sampled signal is accumulated within a loop filter 1320. The loop filter is set for the dynamic response of the slow PLL to aid in the acquisition of a lock by the slow PLL. The PLLs are implemented with op-amp low pass filters that feed ND inputs on microcontrollers, 1302 and 1322, which in turn talk to the DDSs, 1304 and 1306, which provide the energizing signal and local oscillator 1. The microcontroller that controls the energizing DDS 1304 also handles communication with the display. The response of the slow PLL depends upon whether the loop is locked or not. If the loop is unlocked, then the bandwidth is increased so that the loop will lock quickly. In one embodiment, the slow PLL has a damping ratio of 0.7 and a bandwidth of 120 Hz when locked (the Nyquist frequency of the blood pressure waveform), which is approximately ten times slower than the fast PLL.

A DC offset is also added to the signal to allow both a positive and a negative swing. The output of the loop filter is input to an ND input of processor 1322. The processor determines a new frequency and sends the new frequency to the DSSs. The processor offsets the current frequency value of the energizing signal by an amount that is proportional to the amount needed to drive the output of the slow PLL loop filter to a preset value. In one embodiment the preset value is 2.5V and zero in phase. The proportional amount is determined by the PLL's overall transfer function.

The frequency of the energizing signal is deemed to match the resonant frequency of the sensor when the slow PLL is locked. Once the resonant frequency is determined, the physical parameter, such as pressure, is calculated using the calibration parameters associated with the sensor, which results in a difference frequency that is proportional to the measured pressure.

The operation of the slow PLL is qualified based on signal strength. The base unit includes signal strength detection circuitry. If the received signal does not meet a predetermined signal strength threshold, then the slow PLL is not allowed to lock and the bandwidth and search window for the PLL are expanded. Once the received signal meets the predetermined signal strength threshold, then the bandwidth and search window of the slow PLL is narrowed and the PLL can lock. In the preferred embodiment, phase detection and signal strength determination are provided via the "I" (in phase) and "Q" (quadrature) channels of a quadrature mixer circuit. The "I" channel is lowpass filtered and sampled to provide signal strength information to the processing circuitry. The "Q" channel is lowpass filtered and sampled to provide phase error information to the slow PLL.

Avoiding False Locks

The system provides unique solutions to the false lock problem. A false lock occurs if the system locks on a frequency that does not correspond to the resonant frequency of the sensor. There are several types of false locks. The first type of false lock arises due to the pulsed nature of the system. Since the energizing signal is a pulsed signal, it includes groups of frequencies. The frequency that corresponds to a false lock is influenced by the pulse repetition frequency, the Q of the sensor, and the duty cycle of the RF burst. For example, a constant pulse repetition frequency adds spectral components to the return signal at harmonic intervals around the resonant frequency of the sensor, which can cause a false lock. In one embodiment, false locks occur at approximately 600 kHz above and below the resonant frequency of the sensor. To determine a false lock, the characteristics of the signal are examined. For example, pulse repetition frequency dithering and/or observing the slope of the baseband signal are two possible ways of determine a false lock. In one embodiment where the system locks on a sideband frequency, the signal characteristics correspond to a heartbeat or a blood pressure waveform.

The second type of false lock arises due to a reflection or resonance of another object in the vicinity of the system. This type of false lock can be difficult to discern because it generally does not correspond to a heartbeat or blood pressure waveform. The lack of frequency modulation can be used to discriminate against this type of false lock. Changing the orientation of the magnetic loop also affects this type of false lock because the reflected false lock is sensitive to the angle of incidence. The third type of false lock arises due to switching transients caused by switching the PIN diodes and analog switches in the RF path. These transients cause damped resonances in the filters in the receive chain, which can appear similar to the sensor signal. Typically, these types of false locks do not correspond to a heartbeat or blood pressure waveform because they are constant frequency. These types of false locks are also insensitive to orientation of the magnetic loop.

Figure 55A:
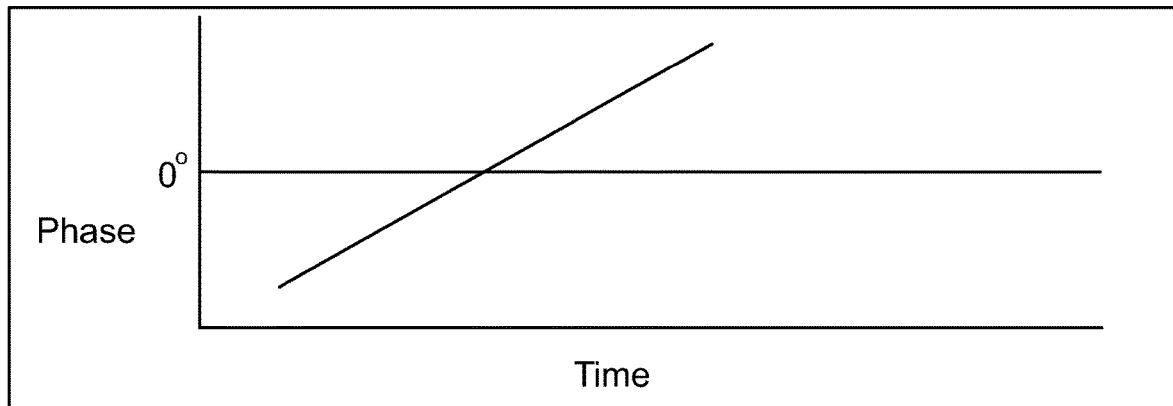
FIGS. 55A and 55B are graphs illustrating exemplary phase difference signals in accordance with an embodiment of the invention.
Figure 55B:
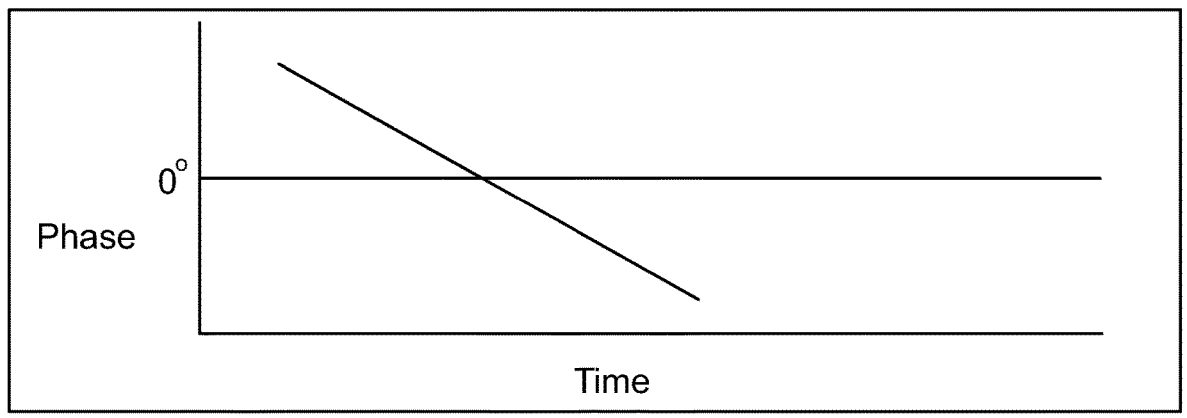

To avoid the first type of false lock, the embodiments herein determine the slope of the baseband signal (the phase difference signal at point 1330). In one embodiment, if the slope is positive, then the lock is deemed a true lock. However, if the slope is negative, then the lock is deemed a false lock. In another embodiment, a negative slope is deemed a true lock and a positive slope is deemed a false lock. The slope is determined by looking at points before and after the phase difference signal goes to zero. The slope can be determined in a number of different ways, including but not limited to, using an analog differentiator or multiple sampling. FIGS. 55A and 55B illustrate a true lock and a false lock respectively, when a positive slope indicates a true lock. In one embodiment, if a false lock is detected, then the signal strength is suppressed so that the signal strength appears to the processor 1322 to be below the threshold and the system continues to search for the center frequency. In other embodiments, any non-zero slope can be interpreted as a false lock resulting in zero signal strength.

Figure 56:
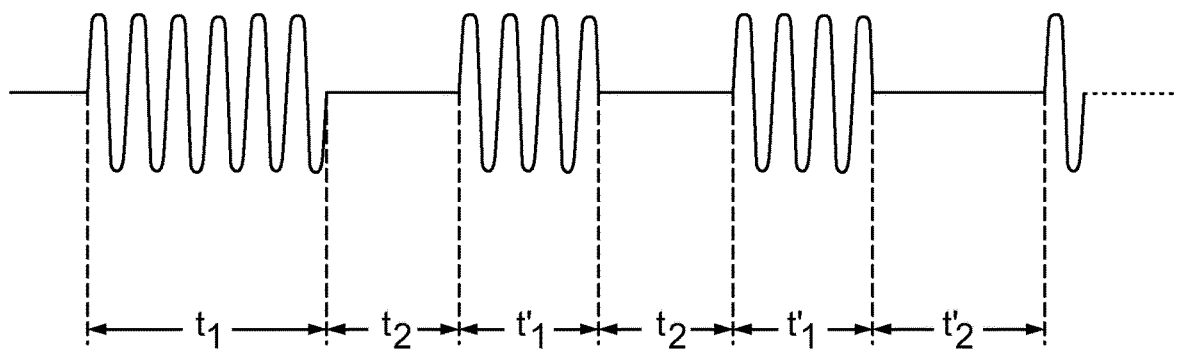
FIG. 56 illustrates frequency dithering in accordance with an embodiment of the invention.

The system can also use frequency dithering to avoid the first type of false lock. Since the spectral components associated with a constant pulse repetition frequency can cause a false lock, dithering the pulse repetition frequency helps avoid a false lock. By dithering the pulse repetition frequency, the spectral energy at the potential false lock frequencies is reduced over the averaged sampling interval. As shown in FIG. 56, the energizing signal includes an on time t1 and an off time t2. The system can vary the on time or the off time to vary the PRF (PRF=1/(t1+t2)). FIG. 56 illustrates different on times (t1, t1') and different off times (t2, t2'). By varying the PRF, the sidebands move back and forth and the average of the sidebands is reduced. Thus, the system locks on the center frequency rather than the sidebands. The PRF can be varied between predetermined sequences of PRFs or can be varied randomly.

Reducing Switching Transients

Figure 57:
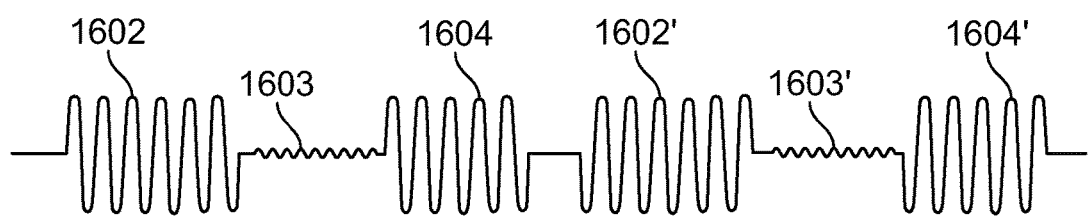
FIG. 57 illustrates phase dithering in accordance with an embodiment of the invention.

The coupling loop switches between an energizing mode and a coupling mode. This switching creates transient signals, which can cause the third type of false lock. Phase dithering is one method used to reduce the switching transients. As shown in FIG. 57, the system receives a switching transient 1603 between the end of the energizing signal 1602 and the beginning of the coupled signal 1604. To minimize the transient, the phase of the energizing signal may be randomly changed. However, changing the phase of the energizing signal requires that the system redefine zero phase for the system. To redefine zero phase for the system, the phase of DDS2 is changed to match the change in phase of the energizing signal. Thus, the phase of the energizing signal 1602' and the coupled signal 1604' are changed, but the phase of the transient signal 1603' is not. As the system changes phase, the average of the transient signal is reduced.

Changing the resonant frequency of the antenna as it is switched from energizing mode to coupling mode also helps to eliminate the switching transients. Eliminating the switching transients is especially important in the present invention because of the characteristics of the coupled signal. The coupled signal appears very quickly after the on period of the energizing signal and dissipates very quickly. In one embodiment, the invention operates in a low power environment with a passive sensor so that the magnitude of the coupled signal is small. However, the invention is not limited to working with a passive sensor.

The coupling loop is tuned to a resonant frequency that is based upon the sensor parameters. Changing the capacitors or capacitor network that is connected to the coupling loop changes the resonant frequency of the antenna. The resonant frequency typically is changed from approximately 1/10% to 2% between energizing mode and coupled mode. In some embodiments, the coupling loop is untuned.

Additional alternative embodiments will be apparent to those skilled in the art to which the present invention pertains without departing from its spirit and scope. For example, the system can operate with different types of sensors, such as non-linear sensors that transmit information at frequencies other than the transmit frequency or sensors that use backscatter modulations. Accordingly, the scope of the present invention is described by the appended claims and is supported by the foregoing description.

Finally, it will be understood that the preferred embodiment has been disclosed by way of example, and that other modifications may occur to those skilled in the art without departing from the scope and spirit of the appended claims.

What is claimed is:

1. An implantable wireless sensor for determining a pressure of a lumen in a body, comprising:
    a sensor body comprising a plurality of substrates, at least a portion of the substrates comprising a first dielectric material;
    an LC resonant circuit contained with the sensor body, a capacitance of the LC resonant circuit configured to vary in response to changes in pressure in the lumen;
    a first anchoring element coupled to a proximal end of the sensor body and a second anchoring element coupled to a distal end of the sensor body, the first and second anchoring elements configured to lodge the sensor body within the lumen; and
    a second dielectric material, different than the first dielectric material, provided over at least a portion of at least one of the plurality of substrates.

2. The sensor of claim 1, wherein a first substrate from the plurality of substrates comprises the first dielectric material.

3. The sensor of claim 2, wherein the LC resonant circuit includes first and second capacitor plates and wherein at least a portion of the first substrate includes a pressure sensitive deflectable region, at least a portion of the first capacitor plate mechanically coupled to the pressure sensitive deflectable region, wherein the deflectable region is configured to deflect in response to changes in pressure in the lumen altering a spacing between the first and second capacitor plates and altering a resonant frequency of the LC resonant circuit.

4. The sensor of claim 1, wherein the second dielectric material is a coating over at least the portion of at least one of the plurality of substrates.

5. The sensor of claim 1, wherein the second dielectric material comprises a low-loss-tangent material to limit lowering of a Q factor of the sensor due to losses associated with fluid surrounding the sensor.

6. The sensor of claim 1, wherein the second dielectric material comprises silicon to limit a dielectric loss of the sensor due to losses associated with fluid surrounding the sensor body.

7. The sensor of claim 1, wherein the LC resonant circuit comprises:
    a first capacitor plate on an internal surface of a first substrate from the plurality of substrates;
    a second capacitor plate disposed in opposed spaced apart relation with the first capacitor plate to form a capacitor (C); and
    an inductor (L) within the cavity, the inductor having one or more windings of a conductive material, the inductor electrically coupled to at least one of the first and second capacitor plates to form the LC resonant circuit.

8. The sensor of claim 1, wherein the first anchoring element includes a first flexible wire loop and the second anchoring element includes a second flexible wire loop.

9. The sensor of claim 1, wherein the first anchoring element includes a wire loop with first and second ends, the first end coupled to the proximal end of the sensor body, the second end coupled to the distal end of the sensor body.

10. The sensor of claim 1, wherein the second anchoring element includes a wire loop with first and second ends, the first end coupled to the proximal end of the sensor body, the second end coupled to the distal end of the sensor body.

* * * * *